United States Patent [19]

Walworth

[11] 4,168,964
[45] Sep. 25, 1979

[54] METHOD FOR THE CONTROL OF UNDESIRED PLANT SPECIES USING IMIDAZO-AS-TRIAZINONES AND TRIAZINE-THIONES

[75] Inventor: Bryant L. Walworth, Pennington, N.J.

[73] Assignee: American Cyanamid Company, Stamford, Conn.

[21] Appl. No.: 932,835

[22] Filed: Aug. 11, 1978

Related U.S. Application Data

[63] Continuation-in-part of Ser. No. 843,173, Oct. 18, 1977, abandoned.

[51] Int. Cl.$^2$ ............................................. A01N 9/22
[52] U.S. Cl. ................................ 71/93; 544/184; 548/343; 548/351; 548/353
[58] Field of Search ..................................... 71/93

[56] References Cited

U.S. PATENT DOCUMENTS

| | | | |
|---|---|---|---|
| 3,759,910 | 9/1973 | Dickore et al. | 71/93 X |
| 3,907,796 | 9/1975 | Jewell et al. | 71/93 X |

OTHER PUBLICATIONS

C. A., 8th Coll. Index for vol. 66–75, 1967–1971 (1973) p. 15656s.
C. A., 9th Coll. Index for vol. 76–85, 1972–1976 (1978), pp. 19522cs–19523cs.

*Primary Examiner*—Joseph Paul Brust
*Attorney, Agent, or Firm*—Harry H. Kline

[57] ABSTRACT

This disclosure describes herbicidal methods for the pre- and postemergence control of undesired mono- and dicotyledonous plants using substituted imidazo[1,5-d]-as-triazin-4(3$\underline{H}$)-ones and substituted imidazo[1,5-d]-as-triazine-4(3$\underline{H}$)-thiones.

13 Claims, No Drawings

METHOD FOR THE CONTROL OF UNDESIRED PLANT SPECIES USING IMIDAZO-AS-TRIAZINONES AND TRIAZINE-THIONES

This application is a continuation-in-part application of my copending application, Ser. No. 843,173, filed Oct. 18, 1977, now abandoned.

BRIEF SUMMARY OF THE INVENTION

This invention relates to a method for the preemergence and postemergence control of undesired monocotyledonous and dicotyledonous plant species comprising applying to the foliage and stems of said plants or to the soil in which the seeds and other propagating organs of said plants germinate and grow a herbicidally effective amount of a compound of formula:

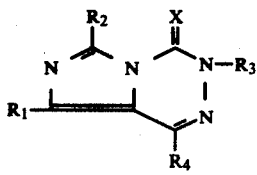

(I)

wherein X is oxygen or sulfur; $R_1$ is hydrogen, alkyl $C_1$–$C_3$, bromo, chloro, or iodo; $R_2$ is hydrogen, alkyl $C_1$–$C_6$, cycloalkyl $C_3$–$C_6$, naphthyl, phenyl, or monosubstituted phenyl wherein said substituent is selected from halogen, alkyl $C_1$–$C_4$, alkoxy $C_1$–$C_4$, haloalkyl $C_1$–$C_3$, dimethylamino and nitro; $R_3$ is hydrogen, alkyl $C_1$–$C_3$, alkenyl $C_3$–$C_4$ or alkynyl $C_3$–$C_4$, and $R_4$ is hydrogen or alkyl $C_1$–$C_4$. A preferred group of compounds may be represented by formula (I) wherein X is oxygen; $R_1$ is methyl, bromo or chloro; $R_2$ is cycloalkyl $C_3$–$C_6$, phenyl or m-tolyl; $R_3$ and $R_4$ are both hydrogen.

The compounds represented by formula (I) above are generally obtainable as white to yellow crystalline materials having characteristic melting points and absorption spectra and which may be purified by recrystallization from common organic solvents such as methanol, ethanol, dimethylformamide, chloroform, and the like. They are appreciably soluble in non-polar organic solvents such as diphenyl ether and carbon tetrachloride but are relatively insoluble in water.

Compounds represented by formula (I) wherein $R_3$ and $R_4$ are both hydrogen may be readily prepared in accordance with the following reaction scheme:

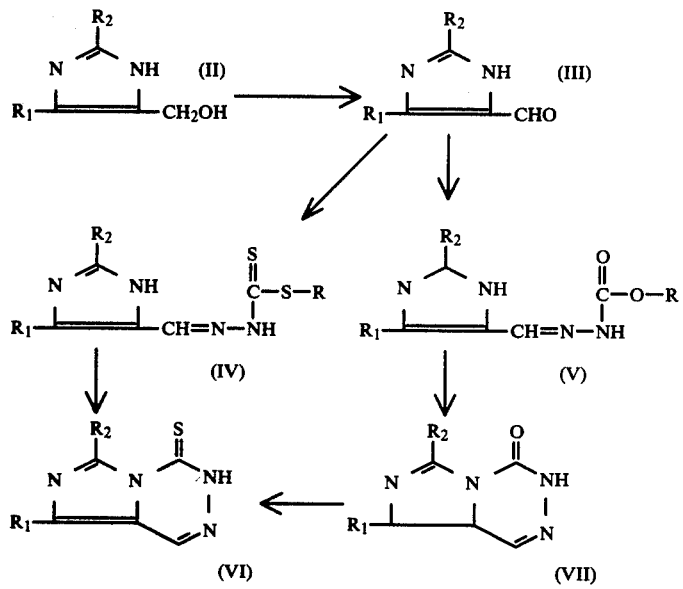

wherein R is methyl or ethyl, $R_1$ is hydrogen or alkyl having up to 3 carbon atoms, and $R_2$ is as hereinabove defined. In accordance with the above reaction scheme, an appropriately substituted 4-imidazolemethanol (II) is oxidized with concentrated nitric acid to provide the corresponding 4-imidazolecarboxaldehyde (III). This oxidation may be carried out by suspending or dissolving each gram of starting material (II) in from about one ml. to about seven ml. of concentrated nitric acid and heating the reaction mixture at steam bath temperature for 2–3 hours. Alternatively, the reaction mixture may first be allowed to stand at room temperature for 8–16 hours and then heated for a short time (15–30 minutes) on the steam bath. The resulting reaction solution is preferably first diluted with water and then neutralized with any convenient base such as caustic, soda ash, or concentrated aqueous ammonia. The precipitated product (III) is removed, washed with water, and purified by recrystallization from common organic solvents such as ethyl acetate, ethanol, and the like. Preferably, the 4-imidazolemethanol (II) may be oxidized with activated manganese dioxide in chloroform, tetrahydrofuran, p-dioxan or t-butanol at a temperature range of 20° to 100° C. for a period of 4–6 hours or until the reaction is complete to provide the 4-imidazocarboxaldehyde (III).

The 4-imidazolecarboxaldehyde (III) may be readily converted to the 3-(4-imidazolylmethylene)dithiocarbazic acid ester (IV) or the 3-(4-imidazolylmethylene)-carbazic acid ester (V) by treatment with methyl or ethyl dithiocarbazinate or with methyl or ethyl carbazate, respectively. This condensation is conveniently carried out in a lower alkanol solvent containing a few drops of glacial acetic acid at a temperature of 25°–75° C. whereupon the product (IV) or (V) forms almost immediately and is removed by filtration. Cyclization of the 3-(4-imidazolylmethylene)-dithiocarbazic acid ester (IV) and the 3-(4-imidazolylmethylene)carbazic acid ester (V) is readily accomplished by heating in a nonpolar high boiling organic solvent such as diphenyl ether at 175°-275° C. for 15-30 minutes whereby the corresponding imidazo[1,5-d]-as-triazine-4(3H)-thiones (VI) and imidazo]1,5-d]-as-triazin-4(3H)-ones (VII) are obtained.

The compounds (VII) wherein $R_1$ is chloro or bromo may be prepared by the chlorination or bromination, respectively, of the corresponding compounds (VII) wherein $R_1$ is hydrogen. This halogenation is accomplished by treating the starting materials with chlorine or bromine in an inert solvent such as chloroform or carbon tetrachloride at steam bath temperature.

The compounds (VII) wherein $R_1$ is iodo may be prepared as follows:

The aldehyde (III) wherein $R_1$ is hydrogen is converted to the dimethyl acetol in methanol/HCl. The dimethyl acetol is iodinated, and then hydrolyzed to yield the corresponding iodoaldehyde (IIIa):

The thus obtained iodoaldehyde (IIIa) is then converted by the above described synthetic route to the desired compound (VII) wherein $R_1$ is iodo and $R_2$ is as hereinabove defined.

Introduction of a $R_4$ substituent into the imidazoastriazinone ring may be accomplished by treatment of aldehyde (III) with alkyl ($C_1$-$C_3$)magnesium bromide followed by Jones oxidation (Jones et al. JCS. 1946, 39; JCS. 1953, 457, 2548, 3019) of the secondary alcohol to the corresponding ketone (VIII) as illustrated below:

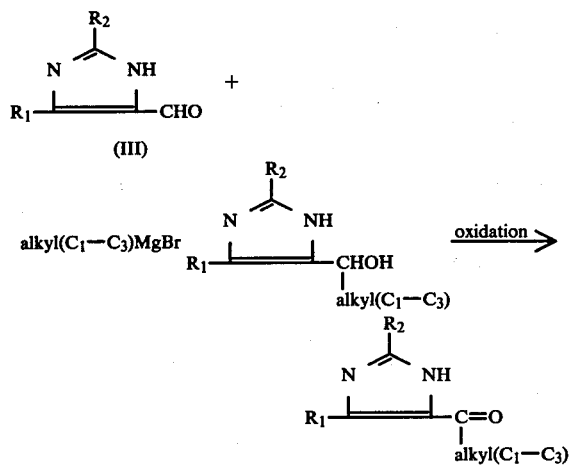

wherein $R_1$ and $R_2$ are as hereinabove defined.

The oxo compounds (VII) can be converted to the thio compounds (VI) by treating the phosphorus pentasulfide in an inert solvent such as pyridine at the reflux temperature. This is a particularly convenient method when $R_1$ is halogen.

Alkylation of formula (I) imidazo-as-triazinone compounds ($R_3$ is hydrogen) at the 3-N-position is accomplished using conventional alkylating agents.

A superior procedure for the 3-N-methylation of a specific compound, 8-methyl-6-phenyl-imidazo[1,5-d]-as-triazin-4(3H)-one is the reaction of same with dimethylformamide dimethylacetol in an inert solvent such as benzene or toluene at about 80°-90° C.

As stated above, the compounds represented by formula (I) are useful herbicidal agents for the control of both monocotyledonous and dicotyledonous plants. They are highly effective for the preemergence control of said undesirable plants when applied at a rate of from about 0.07 kg per hectare to 11.2 kg per hectare to soil containing seeds, seedlings or propagating organs of said broadleaf weeds, or grass plants.

The compounds of formula (I) are also effective for the postemergence control of said undesirable plant species when applied at the rate of from about 0.28 kg per hectare to 11.2 kg per hectare to the foliage of said plants.

Since the imidazo-as-triazinones and imidazo-as-triazinethiones exhibit limited solubility in water, they are generally formulated as wettable powders, emulsifiable concentrates, or flowable (thixotropic) concentrates which are usually dispersed in water or other inexpensive liquid diluent for application as a liquid spray. The above compounds may also be prepared as granular formulations containing, generally, about 10% to 15% by weight of toxicant.

Typically, a wettable powder can be prepared by grinding together about 25% to 80% by weight of a formula (I) compound, about 2% to 5% by weight of a surfactant such as sodium N-methyl-N-oleoyl taurate, alkyl phenoxy polyoxyethylene ethanol, or sodium alkyl naphthalene sulfonate, 5% to 10% by weight of a dispersing agent such as a highly purified sodium lignosulfonate and 25% to 63% by weight of a finely divided carrier such as kaolin, attapulgite, diatomaceous earth, or the like.

A typical formulation prepared in accordance with the above description is as follows:

50% by weight of 8-methyl-6-phenyl-imidazo[1,5-d]-as-triazin-4(3H)-one, 3% by weight of sodium N-methyl-N-oleoyl taurate, 10% by weight of sodium lignosulfonate, and 37% by weight of kaolin.

Flowable (thixotropic) concentrates can be prepared by grinding together about 40% to 60% by weight of the sodium salt of condensed naphthalene sulfonic acids, 2% to 3% by weight of a gelling clay, 2% by weight of propylene glycol, and from 54% to 32% by weight of water.

A typical granular formulation can be prepared by dissolving or dispersing the active compound in a solvent and applying the toxicant to a sorptive or nonsorptive carrier such as attapulgite, corn cob grits, pumice, talc or the like.

The broad spectrum herbicidal activity of formula (I) compounds allows efficient control of undesired vegetation along highways, railroad lines, right-of-ways under power transmission lines and along pipelines and under bridge approaches and/or wherever high degree of control of undesired vegetation is required.

This invention is further illustrated by the following examples.

EXAMPLE 1

5-Methyl-2-phenyl-4-imidazolemethanol

A 100 gm. portion of benzamidine hydrochloride is dissolved in a minimum of water (350 ml.) at room temperature. A 67 gm. portion of freshly distilled 2,3-butanedione is added giving a yellow solution. Adjusting the pH to 6-7 with 2N NaOH gives a solid which is allowed to stand at 0° C. for 2 hours, collected, pressed dry and then washed with 100 ml. of acetone. This material is heated with stirring on a steam bath with 855 ml. of concentrated HCl and 2437 ml. of water for 4 hours giving a solution. Cooling to room temperature overnight and then to 0° C. produces a solid which is collected and air dried. This solid is dissolved in 350 ml. of ethanol, filtered and cooled producing a gel, which is taken up in 250 ml. of 50°-60° C. water, adjusted to pH 5.5 with concentrated NaOH and then to pH 7-8 with solid KHCO$_3$. The mixture is cooled to 0° C. and the product is collected, washed with water, and air dried. This product is recrystallized from one liter of methanol giving the final product, m.p. 197°-199° C.

Alternatively, this product may be prepared by the method of Imback et al., Bull. Soc. Chim. France, 1971, 1052.

EXAMPLE 2

2-Phenyl-4-imidazolemethanol

This product is prepared by the methods of Dziuron and Schunack, Arch. Pharm., 306, 347 (1973) and 307, 46 (1974).

EXAMPLE 3

2-n-Propyl-4-imidazolemethanol

A mixture of 180 gm. of 1,3-dihydroxyacetone dimer, 245 gm. of butyramidine hydrochloride and one liter of liquid ammonia are warmed to 60° C. for 5 hours in a bomb. The mixture is evaporated to dryness and the residue is stirred with 600 ml. of isopropanol. The mixture is filtered and the filtrate is concentrated in vacuo. A 600 ml. portion of 50% saturated aqueous sodium carbonate is added and the mixture is extracted with three 150 ml. portions of tetrahydrofuran. The combined organic layers are washed with 330 ml. of saturated aqueous sodium carbonate. The organic layer is dried over anhydrous sodium sulfate and evaporated to dryness. The residue is twice recrystallized from acetone giving the product, m.p. 95°-101° C.

EXAMPLE 4

2,5-Dimethyl-4-imidazolemethanol hydrochloride

This product is prepared by the method of Imbach et al., Bull. Soc. Chim. France, 1971, 1052.

EXAMPLE 5

2-Methyl-4-imidazolemethanol

A 189 gm. portion of acetamidine hydrochloride and 180 gm. of 1,3-dihydroxyacetone are combined with one liter of liquid ammonia as described in Example 3, giving the desired product, m.p. 115°-117° C.

EXAMPLE 6

4,5-Dimethyl-2-n-propyl-2-imidazoline-4,5-diol hydrochloride

A 112.7 gm. portion of butyramidine hydrochloride is dissolved in 200 ml. of water. A 107 gm. portion of freshly distilled diacetyl is added and the mixture is stirred. The pH is adjusted to 6.5-7.0 with 2 N NaOH and the solution is chilled. The desired product is collected as a solid, m.p. 104°-170° C.

EXAMPLE 7

5-Methyl-2-n-propyl-4-imidazolemethanol

The product from Example 6 is dissolved in 900 ml. of water and 350 ml. of concentrated hydrochloric acid, heated on a steam bath for 5 hours and then chilled. The solution is concentrated in vacuo and a mixture of 100 ml. of acetone and 100 ml. of ethanol is added. The mixture is filtered. The filtrate is evaporated and the residue is dissolved in 50 ml. of water and neutralized with a concentrated solution of K$_2$CO$_3$, until bubbling ceases. The top layer is separated and combined with 5 ml. of methanol. On standing, a precipitate forms. The solid is collected and the filtrate is diluted with acetone to give a second precipitate which is also collected. The solids are combined and recrystallized from hot acetone giving the desired product, m.p. 134°-136° C.

EXAMPLE 8

5-Methyl-4-imidazolemethanol

This product is prepared by the method of Ewins, J. Chem. Soc. 99, 2052 (1911).

EXAMPLE 9

2-(o-Propoxyphenyl)-4-imidazolemethanol

A 130 gm. portion of salicylamide in 500 ml. of ethanol is reacted with 52.4 gm. of sodium methoxide and 164.9 gm. of 1-iodopropane by heating at reflux. The mixture is cooled, precipitated in 1500 ml. of water and the solid is recrystallized from hot ethanol giving o-propoxybenzamide.

A 109 gm. portion of the above compound in 500 ml. of chloroform is reacted with 49.4 ml. of methyl fluorosulfonate by refluxing for 3 hours. After cooling, the mixture is concentrated to an oil. Ether is added forming crystals which are recovered, giving o-propoxy benzimidic acid methyl ester fluorosulfate.

A 180 gm. portion of this latter product and 55.0 gm. of 1,3-dihydroxyacetone in one liter of liquid ammonia are reacted as in Example 3, giving the desired product, m.p. 90°-92° C.

EXAMPLE 10

2-Benzyl-4-imidazolemethanol

A 352 gm. portion of benzyl cyanide, 750 ml. of diethyl ether and 300 ml. of dry ethanol are placed in a two liter, three-necked flask with a magnetic stirrer, drying tube and quick-disconnect gas inlet. The mixture is stirred in an ice bath while hydrochloride gas is bubbled in for one hour. The mixture is placed in a chill room overnight. One liter of ether is added and the mixture is cooled. The precipitate is collected and washed with ether giving ethyliminophenylacetate hydrochloride.

A 272 gm. portion of the above compound and 126 gm. of 1,3-dihydroxyacetone in one liter of liquid ammonia are reacted as in Example 3 giving the desired product, m.p. 134°-135° C.

EXAMPLE 11

2-Methoxymethyl-4-imidazolemethanol

A 307.2 gm. portion of ethyl 2-methoxyacetimidate hydrochloride [Rule, J. Chem. Soc. 113, 9 (1918)] and 180 gm. of 1,3-dihydroxyacetone in one liter of liquid ammonia are reacted as described in Example 3 giving the desired product as an oil. A crystalline picrate salt (m.p. 175°–178° C.) is obtained by heating the oily product and picric acid in water.

EXAMPLE 12

2-tert-Butyl-4-imidazolemethanol

A mixture of 326 gm. of pivalimidic acid methyl ester hydrochloride and 193.5 gm. of 1,3-dihydroxyacetone in 2 liters of liquid ammonia are reacted as desribed in Example 3, giving the desired product, m.p. 212°–221° C.

EXAMPLE 13

2-tert-Butyl-5-methyl-4-imidazolemethanol

In a two liter, three-necked flask, equipped with a magnetic stirrer, drying tube and gas inlet tube, is put 200 gm. of trimethylacetonitrile, 250 ml. of methanol and 500 ml. of diethyl ether. Hydrochloride gas is bubbled in for 2 hours with stirring. The mixture is transferred to a beaker, ether is added and the beaker is covered and stored in a cold room overnight. A 500 ml. portion of ether is added and the solid is filtered and washed with ether, giving white crystals of pivalimidic acid methyl ester hydrochloride.

A 75 gm. portion of the above material is converted to methyl pivalimidate hydrochloride by the method of Brown and Evans, J. Chem. Soc. 1962, 4039.

A 61 gm. portion of this latter product is dissolved in 50 ml. of water with warming and then cooled to room temperature. A 39.3 gm. portion of freshly distilled diacetyl is added and the reaction is continued as described in Examples 6 and 7 giving the desired product as white crystals, m.p. 195.5°–196.5° C.

EXAMPLE 14

2-Benzyl-5-methyl-4-imidazolemethanol

To a solution of 109.6 gm. of α-phenylacetamidine hydrochloride [Luckenbach, Chem. Ber. 17, 1423 (1884)] in 50 ml. of water is added 55.4 gm. of freshly distilled diacetyl. The mixture is stirred, the precipitate is collected, triturated in portions with 200 ml. of acetone and air dried, giving 2-benzyl-4,5-dimethyl-4,5-dihydroxyimidazolidine.

A mixture of 106 gm. of this latter product, 170 ml. of concentrated hydrochloride and 170 ml. of water is reacted as described in Example 7 giving the desired product, m.p. 134°–138° C.

EXAMPLE 15

2-Phenyl-4-imidazolecarboxaldehyde

A 17.4 gm. portion of 2-phenyl-4-imidazolemethanol and 13.4 ml. of concentrated $HNO_3$ are heated on a steam bath for 2½ hours. Three drops of fuming $HNO_3$ are added to start the reaction.. The pH is adjusted to 8 with concentrated aqueous $Na_2CO_3$ and the mixture is cooled to 0° C. overnight. The solid is recovered, washed with water and recrystallized from a mixture of 70 ml. of ethyl acetate and 20 ml. of petroleum ether giving a yellow solid. Treatment of the mother liquor with petroleum ether gives an additional tacky substance which is triturated with isopropanol giving a second solid. These two solids are taken up in hot isopropanol and recrystallized as a yellow solid. This solid is recrystallized from ethanol:water (1:1) giving yellow crystals, m.p. 169°–171.5° C.

EXAMPLE 16

2-n-Propyl-4-imidazolecarboxaldehyde

A solution of 108.6 gm. of 2-n-propyl-4-imidazolemethanol in 107 ml. of concentrated $HNO_3$ is reacted as in Example 15, giving the desired product, m.p. 103.5°–105.5° C.

EXAMPLE 17

2-n-Butyl-4-imidazolecarboxaldehyde

Following the general procedure of Example 15, 2-n-butyl-4-imidazolemethanol is converted to 2-n-butyl-4-imidazolecarboxaldehyde.

EXAMPLE 18

5-Methyl-2-phenyl-4-imidazolecarboxaldehyde

A 102.1 gm. portion of 5-methyl-2-phenyl-4-imidazolemethanol is dissolved in 765 ml. of concentrated $HNO_3$. The solution is cooled in an ice bath and allowed to stand for 16 hours. The solution is heated on a steam bath for 30 minutes, diluted with 2.3 liters of water and neutralized with 50% NaOH while cooling in an ice bath. The solid is collected, dried, recrystallized from 200 ml. of ethanol and then from one liter of 1:2 ethanol:water giving the desired product, m.p. 102°–115° C.

Alternatively, this product may be prepared by the method of Diels and Schleich, Chem. Ber. 49, 1711 (1916).

EXAMPLE 19

5-Ethyl-2-phenyl-4-imidazolecarboxaldehyde

The procedure of Example 18 is repeated substituting an equimolecular amount of 5-ethyl-2-phenyl-4-imidazolemethanol for the 5-methyl-2-phenyl-4-imidazolemethanol employed in that example. There is thus obtained the title compound in equally good yield.

EXAMPLE 20

2,5-Dimethyl-4-imidazolecarboxaldehyde

A 42.2 gm. portion of 2,5-dimethyl-4-imidazolemethanol and 44.8 ml. of concentrated nitric acid are mixed. When the initial reaction subsides, the solution is heated on a steam bath for one hour. The reaction mixture is neutralized with concentrated aqueous sodium carbonate, then concentrated under vacuum. After leaching the residue with 150 ml. of hot ethanol several times, the combined organic solutions are concentrated under vacuum. Chromatographing the residual oil on silica gel gives a solid which is recrystallized from isopropanol-ethyl acetate to give the desired product, m.p. 164.5°–166° C.

EXAMPLE 21

5-Methyl-4-imidazolecarboxaldehyde

This product is prepared by the method of Hubball and Pyman, J. Chem. soc. 1928, 21.

EXAMPLE 22

2-o-Propoxyphenyl-4-imidazolecarboxaldehyde

A 44 gm. portion of 2-(o-propoxyphenyl)-4-imidazolemethanol is placed in a 2 liter round bottom flask together with 500 ml. of chloroform and 100 gm. of manganese dioxide. The mixture is stirred and refluxed for 51 hours. The reaction mixture is filtered while hot. The manganese dioxide is triturated with 500 ml. of hot chloroform and filtered. The two filtrates are combined and evaporated. The solid residue is recrystallized from 200 ml. of hot ethyl acetate and charcoal giving the desired product, m.p. 104°–105° C.

EXAMPLE 23

2-Methyl-4-imidazolecarboxaldehyde

A 143.0 ml. portion of concentrated $HNO_3$ is added in two portions to 119.2 gm. of 2-methyl-4-imidazolemethanol, with cooling after the first portion, and reacted as described in Example 15, giving the desired product, m.p. 170°–176° C.

Alternatively, this product may be made by the methods of Streith et al., Bull. Soc. Chim. France, 4159 (1971) and also Abushanab et al., J. Org. Chem. 40, 3376 (1975).

EXAMPLE 24

2-Benzyl-4-imidazolecarboxaldehyde

A 125 gm. portion of 2-benzyl-4-imidazolemethanol and 500 g. of manganese dioxide in 2 liters of chloroform are reacted as described in Example 22 giving the desired product, m.p. 130°–136° C.

EXAMPLE 25

2-(Methoxymethyl)-4-imidazolecarboxaldehyde

A 145.9 gm. portion of 2-methoxymethyl-4-imidazolemethanol and 137 ml. of concentrated $HNO_3$ are reacted as described in Example 15. After adjusting the pH to 7.0 with concentrated aqueous $Na_2CO_3$, the solution is concentrated under vacuum. Extraction of the residue three times with hot ethanol gives, after combining and concentrating the extracts, a yellow gum. This gum is chromatographed on silica gel. Fractions 7–15 are combined and recrystallized from 120 ml. of isopropanol, treated with charcoal and the desired product is recovered, m.p. 100°–103° C.

EXAMPLE 26

2-Benzyl-5-methyl-4-imidazolecarboxaldehyde

A mixture of 8.79 gm. of 2-benzyl-5-methyl-4-imidazolemethanol and 55.7 ml. of concentrated $HNO_3$ is left at room temperature overnight. The solution is heated for 45 minutes on a steam bath, cooled, the basified with aqueous sodium carbonate. After heating the resulting mixture on a steam bath, it is cooled and the solid collected. Two recrystallizations from ethanol give the desired product, m.p. 171°–173° C.

EXAMPLE 27

2-Benzyl-5-n-propyl-4-imidazolecarboxaldehyde

The general procedure of Example 26 is repeated but replacing the 2-benzyl-5-methyl-4-imidazolemethanol employed in that example with 2-benzyl-5-n-propyl-4-imidazolemethanol.

EXAMPLE 28

5-Methyl-2-n-propyl-4-imidazolecarboxaldehyde

An 80 gm. portion of 5-methyl-2-n-propyl-4-imidazolemethanol is oxidized with 67.3 ml. of concentrated $HNO_3$. A second portion of 101.4 gm. of the above compound is oxidized with 77 ml. of the acid. The reaction mixtures are combined, neutralized and worked up as in Example 25, giving the desired product, m.p. 126°–129° C.

EXAMPLE 29

2-tert-Butyl-4-imidazolecarboxaldehyde

A 7.7 gm. portion of 2-tert-butyl-4-imidazolemethanol is added to 100 ml. of chloroform and 100 ml. of tetrahydrofuran and heated gently. A 25 gm. portion of manganese dioxide is added and the mixture is reacted as described in Example 22 giving the desired product as white crystals, m.p. 194°–195° C.

EXAMPLE 30

2-tert-Butyl-5-methyl-4-imidazolecarboxaldehyde

A 19.76 gm. portion of 2-tert-butyl-5-methyl-4-imidazolemethanol and 16.5 ml. of concentrated $HNO_3$ are reacted as described in Example 25 giving the desired product, m.p. 196°–198° C.

EXAMPLE 31

2-Isobutyl-5-isopropyl-4-imidazolecarboxaldehyde

The procedure of Example 30 is repeated substituting an equimolecular amount of 2-isobutyl-5-isopropyl-4-imidazolemethanol for the 2-tert-butyl-5-methyl-4-imidazolemethanol employed in that example. There is thus obtained the title compound in equally good yield.

EXAMPLE 32

3-(4-Imidazolylmethylene)dithiocarbazic acid methyl ester

A 17.78 gm. portion if imidazole-4-carboxaldehyde (Pyman, J. Chem. Soc. 1916, 186) is dissolved in 200 ml. of hot ethanol. A hot solution 24.4 gm. of methyl dithiocarbazinate [Audrieth et al., J. Org. Chem. 19, 733 (1954)] in 50 ml. of ethanol is added. A precipitate forms immediately and the mixture is heated and stirred for about 10 minutes. The mixture is cooled to 0° C. The precipitate is collected giving yellow crystals, m.p. 259°–261° C.

EXAMPLE 33

3-(2-Phenyl-4-imidazolylmethylene)dithiocarbazic acid methyl ester

A 35 gm. portion of 2-phenyl-4-imidazolecarboxaldehyde is taken up in 250 ml. of hot ethanol. A solution of 22.8 gm. of methyl dithiocarbazinate in 40 ml. of hot ethanol is added and the procedure of Example 32 is followed giving the desired product, m.p. 166°–170° C.

EXAMPLE 34

3-[(5-Methyl-2-phenyl-4-imidazolyl)methylene]dithiocarbazic acid methyl ester

A 60 gm. portion of 5-methyl-2-phenyl-4-imidazolecarboxaldehyde and 36.8 gm. of methyl dithiocarbazinate are reacted as described in Example 32 giving the desired product, m.p. 180°–185° C.

EXAMPLE 35

3-[(5-Ethyl-2-phenyl-4-imidazolyl)methylene]dithiocarbazic acid methyl ester

Following the general procedure of Example 34, 5-ethyl-2-phenyl-4-imidazolecarboxaldehyde is converted to 3-[(5-ethyl-2-phenyl-4-imidazolyl)methylene]dithiocarbazic acid methyl ester.

EXAMPLE 36

3-(2-n-Propyl-4-imidazolylmethylene)dithiocarbazic acid methyl ester

A 60 gm. portion of 2-n-propyl-4-imidazolecarboxaldehyde and 53.7 gm. of methyl dithiocarbazinate are reacted as described in Example 32 giving the desired product, m.p. 95°–104° C.

EXAMPLE 37

3-(2-Methyl-4-imidazolyl-methylene)dithiocarbazic acid methyl ester

A 33 gm. portion of 2-methyl-4-imidazolecarboxaldehyde and 40.3 gm. of methyl dithiocarbazinate are reacted as described in Example 32 giving the desired product, m.p. 274°–279° C.

EXAMPLE 38

3-(5-Methyl-4-imidazolylmethylene)dithiocarbazic acid methyl ester

A 16 gm. portion of 5-methyl-4-imidazolecarboxaldehyde and 19.5 gm. of methyl dithiocarbazinate are reacted as described in Example 32 giving the desired product, m.p. 180° d resolidifies 230°–260° C.

EXAMPLE 39

3-[(2,5-Dimethyl-4-imidazolyl)methylene]dithiocarbazic acid methyl ester

A 20 gm. portion of 2,5-dimethyl-4-imidazolecarboxaldehyde and 20.8 gm. of methyl dithiocarbazinate are reacted as described in Example 32 giving the desired product, m.p. 279°–281° C.

EXAMPLE 40

3-{[2-(Methoxymethyl)-4-imidazolyl]methylene}dithiocarbazic acid methyl ester A 40 gm. portion of 2-(methoxymethyl)-4-imidazolecarboxaldehyde and 38.4 gm. of methyl dithiocarbazinate are reacted as described in Example 32 giving the desired product, m.p. 150°–154° C.

EXAMPLE 41

3-[(5-Methyl-2-n-propyl-4-imidazolyl)methylene]dithiocarbazic acid methyl ester A 20 gm. portion of 5-methyl-2-n-propyl-4-imidazolecarboxaldehyde and 17.7 gm. of methyl dithiocarbazinate are reacted as described in Example 32 giving the desired product, m.p. 175°–179° C.

EXAMPLE 42

3-[(2-benzyl-5-n-Propyl-4-imidazolyl)methylene]dithiocarbazic acid methyl ester The general procedure of Example 41 is repeated but replacing the 5-methyl-2-n-propyl-4-imidazolecarboxaldehyde employed in that example with 2-benzyl-5-n-propyl-4-imidazolecarboxaldehyde.

EXAMPLE 43

3-[(2,5-Dimethyl-4-imidazolyl)methylene]carbazic acid ethyl ester

A 6.2 gm. portion of 2,5-dimethyl-4-imidazolecarboxaldehyde and 6.24 gm. of ethyl carbazate are reacted as described in Example 32 giving the desired product, m.p. 207.5°–210° C. (resolidifies 248°–252° C.)

EXAMPLE 44

3-(2-n-Propyl-4-imidazolylmethylene)carbazic acid ethyl ester

A 7.8 gm. portion of 2-n-propyl-4-imidazolecarboxaldehyde and 6.24 gm. of ethyl carbazate is reacted as described in Example 32 giving the desired product, m.p. 180°–182° C.

EXAMPLE 45

3-(2-Phenyl-4-imidazolylmethylene)carbazic acid ethyl ester

A mixture of 8.16 gm. of 2-phenyl-4-imidazolecarboxaldehyde and 5.52 gm. of ethyl carbazate are reacted as described in Example 32 giving the desired product, m.p. 196°–200° C.

EXAMPLE 46

3-[(5-Methyl-2-phenyl-4-imidazolyl)methylene]carbazic acid ethyl ester

A mixture of 10.25 gm. of 5-methyl-2-phenyl-4-imidazolecarboxaldehyde and 5.72 gm. of ethyl carbazate in 30 ml. of ethanol containing one drop of acetic acid is boiled for 30 minutes. The mixture is dooled to 0° C. and concentrated under an air stream on a steam bath. A 50 ml. portion of carbon tetrachloride is added and the mixture is cooled to 0° C. overnight. The solid is collected giving the desired product, m.p. 209°–211° C.

EXAMPLE 47

3-[(2-o-Propoxyphenyl-4-imidazolyl)methylene]carbazic acid ethyl ester

A 43. gm. portion of 2-o-propoxyphenyl-4-imidazolecarboxaldehyde and 1.98 gm. of ethyl carbazate are reacted as described in Example 32 giving the desired product, m.p. 129°–132° C.

EXAMPLE 48

3-[(2-Benzyl-4-imidazolyl)methylene]carbazic acid ethyl ester

To a 37.2 gm. portion of 2-benzyl-4-imidazolecarboxaldehyde in 200 ml. of ethanol is added 20.8 gm. of ethyl carbazate and a few drops of concentrated acetic acid. The mixture is reacted as described in Example 32 giving the desired product m.p. 184°–185° C.

EXAMPLE 49

3-(2-tert-Butyl-4-imidazolylmethylene)carbazic acid ethyl ester

A 7.6 gm. portion of 2-tert-butyl-4-imidazolecarboxaldehyde and 5.2 gm. of ethyl carbazate in 100 ml. of ethanol are reacted as described in Example 32 giving the desired product, m.p. 194°–197° C.

EXAMPLE 50

3-(2-n-Butyl-4-imidazolylmethylene)carbazic acid ethyl ester

The procedure of Example 49 is repeated substituting an equimolecular amount of 2-n-butyl-4-imidazolecarboxaldehyde for the 2-tert-butyl-4-imidazolecarboxaldehyde employed in that example. There is thus obtained the title compound in equally good yield.

EXAMPLE 51

3-(2-Methyl-4-imidazolylmethylene)carbazic acid ethyl ester

A solution of 16.68 gm. of ethyl carbazate in 50 ml. of hot ethanol is added to a solution of 16.50 gm. of 2-methyl-4-imidazolecarboxaldehyde in 100 ml. of hot ethanol containing 2 drops of acetic acid. The reaction is carried out as described in Example 32 giving the desired product, m.p. 210.5°–211.5° C.

EXAMPLE 52

3-(5-Methyl-4-imidazolylmethylene)carbazic acid ethyl ester

A mixture of 7.0 gm. of 5-methyl-4-imidazolecarboxaldehyde and 7.3 gm. of ethyl carbazate are reacted as described in Example 32 giving the desired product, m.p. 195°–203° C.

EXAMPLE 53

3-{[2-(Methoxymethyl)-4-imidazolyl]methylene}carbazic acid ethyl ester

A 19.60 gm. portion of 2-(methoxymethyl)-4-imidazolecarboxaldehyde and 16.02 gm. of ethyl carbazate are reacted as described in Example 32 giving the desired product, m.p. 186°–190° C.

EXAMPLE 54

3-[(2-Benzyl-5-methyl-4-imidazolyl)methylene]carbazic acid ethyl ester

A 4.08 gm. portion of 2-benzyl-5-methyl-4-imidazolecarboxaldehyde and 2.29 gm. of ethyl carbazate are reacted as described in Example 32 giving the desired product, m.p. 190°–191.5° C.

EXAMPLE 55

3-[(2-tert-Butyl-5-methyl-4-imidazolyl)methylene]carbazic acid ethyl ester

A 6.17 gm. portion of 2-tert-butyl-5-methyl-4-imidazolecarboxaldehyde and 4.20 gm. of ethyl carbazate are reacted as described in Example 32 giving the desired product, m.p. 226°–228.5° C.

EXAMPLE 56

3-[(2-Isobutyl-5-isopropyl-4-imidazolyl)methylene]carbazic acid ethyl ester

Following the general procedure of Example 55, 2-isobutyl-5-isopropyl-4-imidazolecarboxaldehyde is converted to the title compound in equally good yield.

EXAMPLE 57

3-[(5-Methyl-2-n-propyl-4-imidazolyl)methylene]carbazic acid ethyl ester

A 12 gm. portion of 5-methyl-2-n-propyl-4-imidazolecarboxaldehyde and 9.06 gm. of ethyl carbazate are reacted as described in Example 32 giving the desired product, m.p. 184°–188° C.

EXAMPLE 58

Imidazo[1,5-d]-as-triazine-4(3H)-thione

A suspension of 164.5 gm. of 3-(4-imidazolylmethylene)dithiocarbazic acid methyl ester in 1.2 liters of diphenyl ether is heated and stirred at 175° C. until the methylmercaptan evolution subsides (20 minutes). The precipitate obtained on cooling to room temperature is collected and washed with petroleum ether, then acetone. The precipitate is then slurried with 1.2 liters of boiling methanol and filtered while hot to give the desired product, m.p. 217°–273° C.

EXAMPLE 59

8-Methyl-imidazo[1,5-d]-as-triazine-4(3H)-thione

A suspension of 14.39 gm. of 3-(5-methyl-4-imidazolylmethylene)dithiocarbazic acid methyl ester in 100 ml. of diphenyl ether is reacted as described in Example 58 giving the desired product as yellow crystals, m.p. 262°–268° C.

EXAMPLE 60

6-Phenyl-imidazo[1,5-d]-as-triazine-4(3H)-thione

A suspension of 7.05 gm. of 3-(2-phenyl-4-imidazolylmethylene)dithiocarbazic acid methyl ester in 100 ml. of diphenyl ether is reacted as described in Example 58 giving the desired product, m.p. 210° C.

EXAMPLE 61

6-n-Propyl-imidazo[1,5-d]-as-triazine-4(3H)-thione

A 102.2 gm. portion of 3-(2-n-propyl-4-imidazolylmethylene) dithiocarbazic acid methyl ester in 500 ml. of diphenyl ether is reacted as described in Example 58 giving the desired product as a white solid, m.p. 201.5°–203.5° C.

EXAMPLE 62

8-Methyl-6-phenyl-imidazo[1,5-d]-as-triazine-4(3H)-thione

A mixture of 73.4 gm. of 3-[(5-methyl-2-phenyl-4-imidazolyl)methylene]dithiocarbazic acid methyl ester and 500 ml. of diphenyl ether is reacted as described in Example 58 giving the desired product as purple crystals, m.p. 237.5°–239° C.

EXAMPLE 63

8-Ethyl-6-phenyl-imidazo[1,5-d]-as-triazine-4(3H)-thione

The general procedure of Example 62 is repeated but replacing the 3-[(5-methyl-2-phenyl-4-imidazolyl)methylene]-dithiocarbazic acid methyl ester employed in that example with 3-[(5-ethyl-2-phenyl-4-imidazolyl)-methylene]-dithiocarbazic acid methyl ester.

EXAMPLE 64

6,8-Dimethyl-imidazo[1,5-d]-as-triazine-4(3H)-thione

A mixture of 30.26 gm. of 3-[(2,5-dimethyl-4-imidazolyl)methylene]dithiocarbazic acid methyl ester and 125 ml. of diphenyl ether is reacted as described in Example 58 giving a solid which is the desired product, m.p. 287.5°–290° C.

EXAMPLE 65

6-Benzyl-8-methyl-imidazo[1,5-d]-as-triazine-4(3H)-thione

A 2.04 gm. portion of 2-benzyl-5-methyl-4-imidazolecarboxaldehyde is dissolved in 20 ml. of ehtanol containing 2 drops of acetic acid. A 1.34 gm. portion of methyldithiocarbazinate is added, the mixture is boiled for 30 minutes and then cooled to 0° C. overnight. The mixture is evaporated giving 3-[(2-benzyl-5-methylimidazoyl)methylene]dithiocarbazic acid methyl ester as an oil.

A 3.40 gm. portion of the above product is dissolved in 30 ml. of diphenyl ether and heated for 9 minutes at 194°–207° C. The mixture is cooled to room temperature and diluted with hexane. The solid is recrystallized from 150 ml. of methanol and treated with charcoal giving the desired product, m.p. 207°–209.5° C.

EXAMPLE 66

6-Benzyl-8-n-propyl-imidazo[1,5-d]-as-triazine-4(3H)-thione

The procedure of Example 65 is repeated substituting an equimolecular amount of 3-[(2-benzyl-5-n-propylimidazolyl)methylene]dithiocarbazic acid methyl ester for the 3-[(2-benzyl-5-methylimidazolyl)methylene]dithiocarbazic acid methyl ester employed in that example. There is thus obtained the title compound in equally good yield.

EXAMPLE 67

8-Methyl-6-n-propyl-imidazo[1,5-d]-as-triazine-4(3H)-thione

A mixture of 32.12 gm. of 3-[(5-methyl-2-n-propyl-4-imidazolyl)methylene]dithiocarbazic acid methyl ester and 200 ml. of diphenyl ether is reacted as described in Example 58 giving the desired product, m.p. 183°–186° C.

EXAMPLE 68

6-Methyl-imidazo[1,5-d]-as-triazine-4(3H)-thione

A mixture of 53.9 gm. of 3-(2-methyl-4-imidazolylmethylene)dithiocarbazic acid methyl ester and 200 ml. of diphenyl ether is reacted as described in Example 58 giving the desired product, m.p. 280.5°–284° C.

EXAMPLE 69

6-Methoxymethyl-imidazo[1,5-d]-as-triazine-4(3H)-thione

A mixture of 62.4 gm. of 3-{[2-(methoxymethyl)-4-imidazolyl]methylene}dithiocarbazic acid methyl ester and 250 ml. of diphenyl ether is reacted as described in Example 58 giving the desired product m.p. 219.5°–223° C.

EXAMPLE 70

A 10.5 gm. portion of 3-[(2-o-propoxyphenyl-4-imidazolyl)methylene]carbazic acid ethyl ester in 100 ml. of diphenyl-ether is heated on an oil bath with stirring at 255°–265° C. until effervescence subsides. The mixture is cooled to room temperature. The addition of petroleum ether yields a solid which is recrystallized from methanol with the aid of charcoal giving the desired product as a bright yellow solid, m.p. 197°–200° C.

EXAMPLE 71

6-Benzyl-imidazo[1,5-d]-as-triazin-4(3H)-one

A 7.0 gm. portion of 3-[(2-benzyl-4-imidazolyl)methylene]carbazic acid ethyl ester in 50 ml. of diphenyl ether is reacted as described in Example 70 giving the desired product as white crystals, m.p. 215°–217° C.

EXAMPLE 72

6-Phenyl-imidazo[1,5-d]-as-triazin-4(3H)-one

A 7.76 gm. portion of 3-(2-phenyl-4-imidazolylmethylene)carbazic acid ethyl ester in 50 ml. of diphenyl ether is reacted as described in Example 70 giving the desired product, m.p. 245°–248° C.

EXAMPLE 73

8-Methyl-6-phenyl-imidazo[1,5-d]-as-triazin-4(3H)-one

An 8.33 gm. portion of 3-[(5-methyl-2-phenyl-4-imidazolyl)methylene]carbazic acid ethyl ester in 60 ml. of diphenyl ether is heated in an oil bath at 215°–230° C. for 20 minutes. The reaction mixture is diluted to 400 ml. with petroleum ether. The precipitate is collected and recrystallized from 350 ml. of benzene giving the desired product, m.p. 182°–184.5° C.

EXAMPLE 74

6-n-Propyl-imidazo[1,5-d]-as-triazin-4(3H)-one

An 8.75 gm. portion of 3-(2-n-propyl-4-imidazolylmethylene)carbazic acid ethyl ester is 50 ml. of diphenyl ether is reacted as described in Example 70 giving the desired product, m.p. 159°–162.5° C.

EXAMPLE 75

6,8-Dimethyl-imidazo[1,5-d]-as-triazin-4(3H)-one

A mixture of 7.37 gm. of 3-[(2,5-dimethyl-4-imidazolyl)methylene]carbazic acid ethyl ester and 50 ml. of diphenyl ether is reacted as described in Example 70 giving the desired product, m.p. 263°–263.5° C.

EXAMPLE 76

6-tert-Butyl-imidazo[1,5-d]-as-triazin-4(3H)-one

A 6.15 gm. portion of 3-(2-tert-butyl-4-imidazolylmethylene)carbazic acid ethyl ester in 40 ml. of diphenyl ether is reacted as described in Example 70 giving the desired product, m.p. 186°–188° C.

EXAMPLE 77

6-n-Butyl-imidazo[1,5-d]-as-triazin-4(3H)-one

Following the general procedure of Example 76, 3-(2-n-butyl-4-imidazolylmethylene)carbazic acid ethyl ester is converted to the title compound.

EXAMPLE 78

6-Methyl-imidazo[1,5-d]-as-triazin-4(3H)-one

A 27.2 gm. portion of 3-(2-methyl-4-imidazolylmethylene)carbazic acid ethyl ester in 200 ml. of diphenyl ether is reacted as described in Example 70 giving the desired product, m.p. 303°–305.5° C.

EXAMPLE 79

8-Methyl-imidazo[1,5-d]-as-triazin-4(3H)-one

A mixture of 10.26 gm. of 3-(5-methyl-4-imidazolylmethylene)carbazic acid ethyl ester and 100 ml. of diphenyl ether is reacted as described in Example 70 giving the desired product, m.p. 276°–282° C.

EXAMPLE 80

6-Benzyl-8-methyl-imidazo[1,5-d]-as-triazin-4(3H)-one

A mixture of 4.89 gm. of 3-[(2-benzyl-5-methyl-4-imidazolyl)methylene]carbazic acid ethyl ester and 50 ml. of diphenyl ether is reacted as described in Example 70 giving the desired product, m.p. 244°–247° C.

EXAMPLE 81

6-tert-Butyl-8-methyl-imidazo[1,5-d]-as-triazin-4(3H)-one

A mixture of 5.11 gm. of 3[(2-tert-butyl-5-methyl-4-imidazolyl)methylene]carbazic acid ethyl ester and 50 ml. of diphenyl ether is reacted as described in Example 70 giving the desired product, m.p. 198°–200° C.

EXAMPLE 82

6-Isobutyl-8-isopropyl-imidazo[1,5-d]-as-triazin-4(3H)-one

The general procedure of Example 81 is repeated but replacing the 3-[(2-tert-butyl-5-methyl-4-imidazolyl)-methylene]carbazic acid ethyl ester employed in that example with 3-[(2-isobutyl-5-isopropyl-4-imidazolyl)-methylene]carbazic acid ethyl ester.

EXAMPLE 83

8-Methyl-6-n-propyl-imidazo[1,5-d]-as-triazin-4(3H)-one

A 14.50 gm. portion of 3-[(5-methyl-2-n-propyl-4-imidazolyl)methylene]carbazic acid ethyl ester and 100 ml. of diphenyl ether are reacted as described in Example 70 giving the desired product, m.p. 129.5°131.5° C.

EXAMPLE 84

6-Methoxymethyl-imidazo[1,5-d]-as-triazin-4(3H)-one

A mixture of 25.9 gm. of 3-{[2-(methoxymethyl)-4-imidazolyl]methylene}carbazic acid ethyl ester and 125 ml. of diphenyl ether is reacted as described in Example 70 giving the desired product, m.p. 200°–205° C.

EXAMPLE 85

8-Bromo-6-phenyl-imidazo[1,5-d]-as-triazin-4(3H)-one

A 3.0 portion of 6-phenyl-imidazo[1,5-d]-as-triazin-4(3H)-one is stirred with 100 ml. of chloroform. The mixture is heated slightly and a solution of one ml. of bromine in 10 ml. of chloroform is slowly dripped into the reaction mixture. The mixture is refluxed for one hour, cooled to room temperature, and filtered. To the solid is added aqueous $Na_2CO_3$ and chloroform and the mixture is shaken in a separatory funnel. The remaining solid and the organic phase are combined and evaporated to a steam bath. Methanol and 2-propanol are added and the mixture is treated twice with charcoal. Cooling gives the desired product as a solid, m.p. 192°–194° C.

EXAMPLE 86

8-Bromo-6-n-butyl-imidazo[1,5-d]-as-triazin-4(3H)-one

The procedure of Example 85 is repeated substituting an equimolecular amount of 6-n-butyl-imidazo[1,5-d]-as-triazin-4(3H)-one for the 6-phenyl-imidazo[1,5-d]-as-triazin-4(3H)-one employed in that example. There is thus obtained the title compound in equally good yield.

EXAMPLE 87

8-Chloro-6-phenyl-imidazo[1,5-d]-as-triazin-4(3H)-one

A 5.0 gm. portion of 6-phenyl-imidazo[1,5-d]-as-triazin-4(3H)-one is mixed with 100 ml. of chloroform on a steam bath while chlorine gas is bubbled through the mixture. A 25 ml. portion of methanol is added. Chlorine is again bubbled through for 10–15 minutes. The mixture is cooled to room temperature, transferred to a separatory funnel, washed with aqueous $Na_2CO_3$, aqueous $NaHSO_3$ and finally with water. The mixture is evaporated to 75 ml. on a steam bath, cooled and filtered. The filtrate is evaporated overnight giving a solid. This solid is dissolved in 30 ml. of hot chloroform and filtered. The filtrate is treated with charcoal and 2-propanol is added giving the desired product as a solid, m.p. 201°–203° C.

EXAMPLE 88

8-Chloro-6-benzyl-imidazo[1,5-d]-as-triazin-4(3H)-one

Following the general procedure of Example 86, 6-benzyl-imidazo[1,5-d]-as-triazin-4(3H)-one is chlorinated to give the title compound.

EXAMPLE 89

8-Methyl-6-phenyl-imidazo[1,5-d]-as-triazin-4(3H)-thione

To a solution of 4.5 gm. of 8-methyl-6-phenylimidazo-[1,5-d]-as-triazin-4(3H)-one in 100 ml. of pyridine is added 5 gm. of phosphorus pentasulfide. The reaction mixture is heated at 100° C. for 8 hours, filtered, and poured into dilute hydrochloric acid. The precipitated product is isolated by filtration, washed with water, and dried.

EXAMPLE 90

8-Bromo-6-phenyl-imidazo[1,5-d]-as-triazine-4(3H)-thione

The procedure of Example 89 is repeated but substituting an equimolar amount of 8-bromo-6-phenyl-imidazo [1,5-d]-as-triazin-4(3H)-one for the 8-methyl-6-phenyl-imidazo[1,5-d]-as-triazin-4(3H)-one employed in that example.

EXAMPLE 91

8-Chloro-6-phenyl-imidazo[1,5-d]-as-triazin-4(3H)-one

The use of 5-chloro-2-phenyl-4-imidazolecarboxaldehyde and ethyl carbazate in the procedure of Example 46 affords 3-[(5-chloro-2-phehyl-4-imidazolyl)methylene]-carbazic acid ethyl ester, which is converted to the title compound by heating in diphenyl ether as in Example 70.

EXAMPLE 92

Preparation of Amidines

The amidines prepared by known procedures and used as starting materials for the preparation of imidazo-as-triazinones are listed in Table I below, characterized as hydrochlorides unless otherwise noted. Known literature references are also given.

TABLE I

Amidines Prepared by Known Procedures $$R_2-\underset{NH_2}{\overset{NH}{\diagup\!\!\!\!\diagdown}} \cdot HCl$$

| $R_2$ | m.p.(°C.) | Reference |
|---|---|---|
| 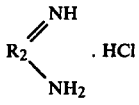 | 283–284(d) | Schaefer et al. J.O.C. 26, 412(1961) m.p. given as 285°–287° C. |
| 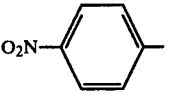 | 209–213(d) | Fanta et al., JACS. 78, 1434 (1956) m.p. gven as 215°–216° C. |
| 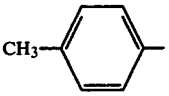 | 217–218.5(d) | Rogana et al. JACS. 97(23)6844(1975) m.p. given as 218°–220° C. |
| 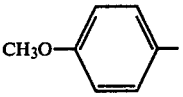 | 235–238(d) | m.p. given as 243°–245° C. (½H₂O) |
| 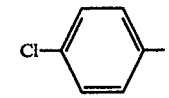 | 181–185(d) | Ekeley et al. JACS. 57, 381(1935) m.p. given as 185.5° C. |
| 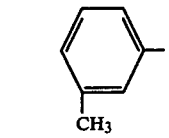 | 251–254(d) | Weintraub et al. JOC. 33(4)1679(1968) m.p. given as 256°–258.5° C. |
| 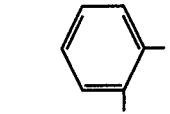 | 100–110 resolidifies 227–230(d) | |
|  | 222–224 | |
| 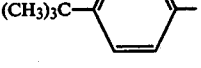 | 188–189(d) | |
| $C_6H_{13}$— | 54–55 Hygroscopic solid | |
| $C_4H_9$— | picrate: 191–192(d) | JCS. 2991(1931) m.p. given as 192°–193° C. |
|  | 122–124 | U.S. Pat. No. 3,454,575 described as HBr salt |
|  | hygroscopic solid | U.S. Pat. No. 3,454,575 described as HBr salt |

EXAMPLE 93

Cis and trans-4,5-Dimethyl-2-m-tolyl-2-imidazoline-4,5-diol hydrochloride 2,3-Butanedione (7.3 ml., 0.084 mole) is added dropwise to a cold slurry of m-toluamidine hydrochloride (13.6 gm., 0.0797 mole) in water (35 ml.) and stirred at room temperature for 15 minutes. The precipitated product is collected by filtration and washed with acetone to give 12.2 gm., m.p. 135°–137° C.

Analysis calculated for $C_{12}H_{17}N_2O_2Cl$: C 56.14; H 6.67; N 10.91; Cl 13.81 Found: C 55.92; H 6.66; N 10.94; Cl 1409.

Additional 2-substituted cis and trans-4,5-dimethylimidazoline 4,5-diol hydrochlorides prepared by the above procedure, their melting points, and deviations from the above procedure, are listed in Table II below.

TABLE II

R₂—[imidazoline structure with CH₃, OH, CH₃, OH, HCl]

| R₂ | m.p. (°C.) | Remarks |
|---|---|---|
| O₂N—C₆H₄— | >160 (d) | Reactants added at 55°–60° C. |
| CH₃—C₆H₄— | 138–139 (d) | |
| CH₃O—C₆H₄— | 132–135 (d) | |
| o-CH₃-C₆H₄— | | |
| Cl—C₆H₄— | 171–174, clear at 195 (d) | Reactants added at 40°–50° C. |
| 2-naphthyl | | Optimal reaction temperature is 40° C. |
| C₄H₉ | 121–124 (d) | |
| C₆H₁₃— | 102–104 (d) | |
| cyclopropyl | 120–122 (d) | |
| cyclopentyl | 129–131 (d) | |
| cyclohexyl | 147–149 (d) | |

EXAMPLE 94

5-Methyl-2-m-tolyl-4-imidazolemethanol

A mixture of cis and trans-4,5-dimethyl-2-m-tolyl-2-imidazoline-4,5-diol hydrochloride (9.0 gm., 0.035 mole) and 3 N hydrochloric acid (135 ml.) is stirred and heated on a steam bath for 2.5 hours and then stirred at 0°–5° C. for 0.75 hours. The reaction mixture is filtered to yield 7.4 gm. (0.031 mole) of a white solid. The solid is treated with base to afford the title compound, m.p. 190°–192° C.(d).

Analysis calculated for $C_{12}H_{14}N_2O$: C 71.26; H 6.98; N 13.85; Found: C 70.94; H 7.07; N 13.92.

Additional imidazolemethanol compounds prepared by the above procedure are listed in Table III below.

TABLE III

R₂—[imidazole structure with CH₂OH and CH₃]

| R₂ | m.p.(°C.) | Calculated | Found |
|---|---|---|---|
| O₂N—C₆H₄— | 215–216(d) | C 56.65 / H 4.75 / N 18.02 | C 56.64 / H 4.73 / N 17.74 |
| CH₃—C₆H₄— | >150(d) | C 71.26 / H 6.98 / N 13.85 | C 70.86 / H 6.97 / N 13.60 |
| CH₃—C₆H₄—·HCl | 111–114 | | |
| CH₃O—C₆H₄— | 205–207 | C 66.04 / H 6.47 / N 12.83 | C 65.75 / H 6.88 / N 12.90 |
| CH₃O—C₆H₄—·HCl | 132–134(d) | | |
| Cl—C₆H₄—·H₂O | 205–207(d) | C 59.33 / H 4.98 / N 12.58 / Cl 15.92 | C 59.73 / H 5.22 / N 12.44 / Cl 16.05 |
| Cl—C₆H₄—·HCl | >170(d) | C 47.67 / H 5.09 / N 10.11 / Cl 25.58 | C 48.15 / H 5.18 / N 9.86 / Cl 25.39 |
| o-CH₃-C₆H₄— | 175–177 | | |
| 2-naphthyl | 188–190(d) | | |
| 2-naphthyl·HCl | >120(d) | | |
| C₄H₉ | syrup | | |
| C₆H₁₃ | syrup | | |
| cyclopropyl | 104–106(d) | | |
| cyclopentyl | 115–120(d) | | |
| cyclohexyl | 182–183(d) | C 68.00 / H 9.34 / N 14.42 | C 67.73 / H 9.55 / N 13.87 |

EXAMPLE 95

Preparation of 2-substituted 5-methyl-4-imidazolecarboxaldehyde

Method A

5-Methyl-2-m-tolyl-4-imidazolecarboxaldhyde

A mixture of 5-methyl-2-m-tolyl-4-imidazolemethanol (13.0 gm., 0.064 mole), activated manganese dioxide (65 gm.) and methylene chloride (200 ml.) is stirred at room temperature for 20 hours. The reaction mixture is then filtered, the solvent removed in vacuo to afford 9.1 gm. (0.045 mole) of peach-colored solid.

Method B

5-Methyl-2-(p-nitrophenyl)-4-imidazolecarboxaldehyde

A mixture of 5-methyl-2-(p-nitrophenyl)-4-imidazolemethanol (2.9 gm., 0.012 mole) and 70% nitric acid (20 ml.) is stirred at 50° C. for 3 hours, followed by dilution with water and neutralization with base. The precipitated yellow solid is collected by filtration to yield 2.4 gm. (0.011 mole) of title product, dec. >270° C.

Analysis calculated for $C_{11}H_9N_3O_3$: C 57.14; H 3.92; N 18.17; Found: C 56.69; H 3.96; N 18.08.

Method C

Preparation of 2-alkyl(cycloalkyl)-5-methylimidazole-4-carboxaldehydes

A mixture of 2-alkyl(cycloalkyl)-5-methyl-4-imidazolemethanol (0.1 mole), activated manganese dioxide (0.5 mole) and chloroform (500 ml.) is stirred and refluxed for two hours, then stirred overnight (appr. 15–16 hours) at room temperature. The mixture is filtered through a bed of filter-aid, the solution evaporated to dryness and the residue recrystallized from the appropriate solvent.

By one or the other methods of preparation described above, a number of 2-substituted 5-methyl-4-imidazolecarboxaldehydes are made. The compounds, their method of preparation, melting points and analytical data are given in Table IV below.

TABLE IV structure: imidazole with H on N, CHO at position 4, CH3 at position 5, R2 at position 2

| R2 | Method* | m.p.(°C.) | Analysis Calculated | Analysis Found |
|---|---|---|---|---|
| CH3—C6H4— | A | 192–194(d) | N 13.99 | N 14.28 |
| CH3O—C6H4— | A | 161–163(d) | C 66.65<br>H 5.59<br>N 12.95 | C 66.52<br>H 5.86<br>N 13.08 |
| Cl—C6H4— | A | 237–239(d) | C 59.88<br>H 4.11<br>N 12.70<br>Cl 16.07 | C 59.30<br>H 4.17<br>N 12.61<br>Cl 16.23 |
| o-CH3-C6H4— | A | 140–143(d) | C 71.98<br>H 6.04<br>N 13.99 | C 71.61<br>H 6.37<br>N 13.87 |
| naphthyl | A | 197–199(d) | C 76.25<br>H 5.12<br>N 11.86 | C 76.15<br>H 5.25<br>N 11.81 |
| $C_4H_9$— | A | 83–84 | C 65.03<br>H 8.49<br>N 16.85 | C 64.85<br>H 7.96<br>N 17.04 |
| $C_6H_{13}$— ½$H_2O$ | A | syrup | C 65.00<br>H 9.42<br>N 13.79 | C 65.72<br>H 9.15<br>N 13.64 |
| cyclopropyl | A | 104–109 | | |
| cyclobutyl | A | 114–120 | | |
| cyclohexyl | A | 159–162 | C 68.72<br>H 8.39<br>N 14.57 | C 69.06<br>H 8.44<br>N 14.43 |

*Preferred solvent is chloroform, p-dioxane and tert-butanol are also used.

EXAMPLE 96

α-Methyl-2-phenyl-4-imidazolemethanol

Methyl magnesium bromide (15.3 ml., 2.5 molar in ether) is added dropwise to a solution of 2-phenyl-4-imidazolecarboxaldehyde (3.0 gm. 0.017 mole) in dry tetrahydrofuran (45 ml.; dried over a molecular sieve) while the temperature of the reaction mixture is maintained with cooling at 25° C. The mixture is stirred for 2 hours, and then decomposed by adding a large volume of water dropwise. The mixture is extracted with ether (3×75 ml.), the ethereal extract is partially evaporated to yield a white precipitate, the crystalline alcohol, m.p. 197°–198° C.

Analysis calculated for $C_{11}H_{12}N_2O$: C 70.19; H 6.43; N 14.88; Found: C 70.10; H 6.68; N 14.90.

EXAMPLE 97

α,5-Dimethyl-2-phenyl-4-imidazolemethanol

α,5-Dimethyl-2-phenyl-4-imidazolemethanol is prepared from 5-methyl-2-phenyl-4-imidazolecarboxaldehyde (37.0 gm., 0.199 mole) by the method of Example 96. The product (38.4 gm., 95.5%) is obtained as a white crystalline solid, m.p. 189°–190° C.

EXAMPLE 98

Methyl 2-phenyl-4-imidazolyl ketone

Jones reagent [5 ml.; a solution of chromium trioxide (10.3 gm.) in a mixture of sulfuric acid (8.7 ml.) and water (30 ml.)] is added at 0°–5° C. over 1 hours to a solution of methyl-2-phenyl-4-imidazolemethanol (3.0 gm., 0.016 mole) in acetone (25 ml.). The temperature is allowed to rise to 20° C. for 30 minutes then water (150 ml.) is added. The mixture is stirred for 1 hour and the precipitated solid collected by filtration. The solid is treated with 2 N hydrochloric acid (15 ml.), stirred 5 minutes, and is then neutralized with 10% sodium hydroxide. The aqueous mixture is extracted with methylene chloride (3×75 ml.). Removal of the methylene chloride yields the ketone as a white crystalline solid (1.73 gm.), m.p. 158°–158.5° C.

Analysis calculated for $C_{11}H_{12}N_2O$: C 70.95; H 5.41; N 15.04; Found: C 70.34; H 5.52; N 15.03.

EXAMPLE 99

Methyl-5-methyl-2-phenyl-4-imidazolyl ketone

By the method of Example 98 methyl-5-methyl-2-phenyl-4-imidazolyl ketone is prepared from α,5-dimethyl-2-phenyl-4-imidazolemethanol (12.0 gm., 0.059 mole). The product is obtained as a pale yellow crystalline solid (0.88 gm., 58.3%), m.p. 188°–190° C.

Analysis calculated for $C_{12}H_{12}N_2O$: C 71.98; H 6.04; N 13.99; Found: C 71.30; H 6.29; N 13.40.

EXAMPLE 100

2-Phenyl-5-imidazolecarboxaldehyde dimethyl acetal

A solution of 2-phenyl-5-imidazolecarboxaldehyde (6.10 gm., 0.035 mole) in methanol (200 ml) is cooled in an ice bath and then saturated with hydrogen chloride. The reaction mixture is stirred overnight (appr. 15–16 hours) and added slowly to cold 6 N sodium hydroxide (200 ml.). The solution is neutralized with concentrated hydrochloric acid and the precipitated solid collected by filtration (7.56 gm., 0.035 mole). Recrystallization from chloroform yields white needles, m.p. 158°–160° C.

Analysis calculated for $C_{12}H_{14}N_2O_2$: C 66.03; H 6.48; N 12.83; Found: C 65.38; H 7.01; N 12.63.

EXAMPLE 101

4-Iodo-2-phenyl-5-imidazolecarboxaldehyde dimethyl acetal, and 4-iodo-2-phenyl-5-imidazolecarboxaldehyde A solution of iodine (10.25 gm., 0.0404 mole) in methanol (200 ml.) is added with stirring to a solution of 2-phenyl-5-imidazolecarboxaldehyde dimethyl acetal (7.56 gm., 0.035 mole) in methanol (200 ml.), water (20 ml.) and 6 N sodium hydroxide (13 ml.). The reaction mixture is stirred for 5 hours, and then concentrated in vacuo to about 75 ml. volume. Water (200 ml.) is added and the precipitated 4-iodo-2-phenyl-5-imidazolecarboxaldehyde dimethyl acetal (2.82 gm., 0.0082 mole) is collected by filtration, m.p. 144°–148.5° C.(d).

The aqueous filtrate is acidified with concentrated hydrochloric acid and the precipitated 4-iodo-2-phenyl-5-imidazolecarboxaldehyde (5.51 gm., 0.018 mole) is collected by filtration, m.p. 208°–210° C.(d).

Recrystallization of 4-iodo-2-phenyl-5-imidazolecarboxaldehyde dimethyl acetal from methyl cyclohexane/THF yields white crystals, m.p. 152°–153.5° C.

Analysis calculated for $C_{12}H_{13}N_2O_2I$: C 41.88; H 3.82; N 8.14; Found: C 41.82; H 4.19; N 8.34.

Recrystallization of 4-iodo-2-phenyl-5-imidazolecarboxaldehyde from ethyl acetate yields a white solid, m.p. 211.5°–212.5° C.

Analysis calculated for $C_{10}H_7N_2OI$: C 40.29; H 2.37; N 9.39; Found: C 40.19; H 2.37; N 9.34.

EXAMPLE 102

General methods for the preparation of 3-[(2-substituted-5-methyl-4-imidazolyl)methylene]carbazic acid methyl esters

A

3-[(5-methyl-2-m-tolyl-4-imidazolyl)methylene]carbazic acid, methyl ester

A mixture of 5-methyl-2-m-tolyl-4-imidazolecarboxaldehyde (6.9 gm., 0.034 mole), methyl carbazate (3.1 gm., 0.034 mole), methylene chloride (70 ml.) and acetic acid (1 drop) is refluxed for 1 hour. The precipitated white solid is collected by filtration to yield 7.1 gm. (0.026 mole), m.p. 162°–164° C.

By the above procedure several 2-aryl analogs of the compound are prepared. These compounds, their melting points and analyses are listed in Table V below.

B Preparation of 3-[(2-alkyl or cycloalkyl-5-methyl-4-imidazolyl)methylene]carbazic acid, methyl esters A mixture of 2-alkyl(cycloalkyl)-5-methylimidazole-4-carboxaldehyde (0.1 mole), methyl carbazate (0.1 mole), toluene (60 ml.) and acetic acid (0.5 ml.) is refluxed for 2 hours. The reaction mixture is then cooled down, the solids are collected by filtration, and are recrystallized from the appropriate solvent.

The 2-alkyl and cycloalkyl compounds prepared by the above procedure are listed in Table V below.

TABLE V $$\begin{array}{c} H \\ | \\ R_2 - \underset{N}{\overset{N}{\diagdown}} \underset{R_1}{\diagup} - CH = N - NH - CO_2CH_3 \end{array}$$

| $R_2$ | $R_1$ | m.p. (°C.) | Analysis Calculated | Found |
|---|---|---|---|---|
| $O_2N-\langle\phantom{O}\rangle-$ | $CH_3$ | 264–265(d) | C 51.49<br>H 4.32<br>N 23.09 | C 50.96<br>H 4.33<br>N 23.21 |
| $CH_3-\langle\phantom{O}\rangle-$ | $CH_3$ | 226–227(d) | | |
| $CH_3O-\langle\phantom{O}\rangle-$ | $CH_3$ | 176–178(d) | C 58.32<br>H 5.59<br>N 19.43 | C 58.01<br>H 5.60<br>C 19.23 |
| $Cl-\langle\phantom{O}\rangle-$ | $CH_3$ | 234–236(d) | C 53.34<br>H 4.47<br>N 19.14 | C 52.95<br>H 4.42<br>N 18.99 |
| (o-tolyl, CH₃) | $CH_3$ | 160–162(d) | | |
| (naphthyl) | $CH_3$ | >170(d) | | |
| $C_4H_9-$ | $CH_3$ | 189.5–190.5(d) | C 55.44<br>H 7.61<br>N 23.52 | C 55.09<br>H 7.71<br>N 23.54 |
| $C_6H_{13}-$ | $CH_3$ | 164–165(d) | C 58.62<br>H 8.33<br>N 21.04 | C 58.34<br>H 7.78<br>N 20.83 |
| cyclopropyl | $CH_3$ | 184–186(d) | C 54.04<br>H 6.35<br>N 25.21 | C 54.25<br>H 6.49<br>N 25.53 |
| cyclobutyl | $CH_3$ | 196–197(d) | | |
| cyclohexyl | $CH_3$ | 193–194(d) | C 59.07<br>H 7.63<br>N 21.20 | C 58.62<br>H 7.61<br>N 20.80 |
| $Cl-\langle\phantom{O}\rangle-\cdot H_2O$ | Cl | 147–148 | C 43.5<br>H 3.63<br>N 16.9<br>Cl 21.14 | C 45.04<br>H 4.05<br>N 16.09<br>Cl 20.73 |

EXAMPLE 103

3-[1(5-iodo-2-phenyl-4-imidazolyl)ethylidene]carbazic acid methyl ester

A solution of 4-iodo-2-phenyl-5-imidazolecarboxaldehyde (5.21 gm., 0.017 mole) in a mixture of methanol (50 ml.), toluene (250 ml.), acetic acid (1 ml.) and methyl carbazate (1.73 gm., 0.019 mole) is refluxed for 24.5 hours. The solution is then heated for an additional hour, allowing solvent (100 ml.) to distill off. The remaining solvent is then removed in vacuo. The solids are extracted with methylene chloride (300 ml.), and the extract washed with water (3×200 ml.). At this point the product crystallizes and is collected by filtration (2.16 gm., 0.0056 mole). Evaporation of the filtrate yields additional product (3.44 gm., 0.0093 mole). Recrystallization from methanolmethylene chloride yields white crystals, m.p. 145°–147° C.(d).

EXAMPLE 104

3-[1-(5-methyl-2-phenyl-4-imidazolyl)ethylidene]carbazic acid, methyl ester

Methyl 5-methyl-2-phenyl-4-imidazolyl ketone (4.5 gm., 0.023 mole) is refluxed with methyl carbazate (2.4 gm., 0.023 mole) in toluene (112 ml.) for 5 hours. The toluene is removed, and the solid washed with water (3×50 ml.). The solid is recrystallized from methanol to yield the product (1.28 gm., 20.9%), m.p. 201°–201.5° C.

Analysis calculated for $C_{14}H_{16}N_4O_2$: C 61.75; H 5.92; N 20.57; Found: C 60.05; H 6.25; N 19.96.

EXAMPLE 105

3-[1-(2-phenyl-4-imidazolyl)ethylidene]carbazic acid methyl ester

By the method of Example 104, the title product is prepared from methyl-2-phenyl-4-imidazolyl ketone and methyl carbazate. The product is obtained in 91% yield, m.p. 226.5°–227° C.

Analysis calculated for $C_{13}H_{14}N_4O_2$: C 60.46; H 5.46; N 21.69; Found: C 60.59; H 5.60; N 21.89.

EXAMPLE 106

Preparation of 6-(aryl)-8-methyl-imidazo[1,5-d-]-as-triazin-4(3H)-ones

Method A

8-Methyl-6-m-tolyl-imidazo[1,5-d]-as-triazine-4(3H)-one

A mixture of 3-[(5-methyl-2-m-tolyl-4-imidazolyl)-methylene]carbazic acid, methyl ester (5.1 gm., 0.019 mole) and o-dichlorobenzene (75 ml.) is heated slowly (45 minutes) to reflux, refluxed for 1.5 hours, then stirred at room temperature overnight (appr. 15–16 hours). The reaction mixture is filtered to afford 3.9 gm. (0.016 mole) title product. Recrystallization from o-dichlorobenzene yields partially solvated product, m.p. 188°–198° C.

By substituting 3-{[5-methyl-2-(α,α,α-trifluoromtolyl)-4-imidazolyl]methylene}carbazic acid, methyl ester for 3-[(5-methyl-2-m-tolyl-4-imidazolyl)methylene]carbazic acid, methyl ester in the above reaction, 8-methyl-6-(α,α,α-trifluoro-m-tolyl)-imidazo[1,5-d]-as-triazin-4(3H)-one can be obtained.

Method B

8-Methyl-6-(p-nitrophenyl)-imidazo[1,5-d]-as-triazine-4(3H)-one, monohydrate

3-{[2-(p-nitrophenyl)-5-methyl-4-imidazolyl]methylene}carbazic acid, methyl ester (2.5 gm., 0.082 mole) is immersed in diphenyl ether (25 ml.) at 240° C. for 20 minutes, then stirred in an ice bath for 1 hour. The reaction mixture is diluted with ether and filtered to afford 2.2 gm. (0.008 mole) title product. The product is purified via an acetone soxhlet extraction to give a yellow solid, m.p. 295°–297° C.

Analysis calculated for $C_{12}H_{11}N_5O_4$: C 49.83; H 3.83; N 24.21; Found: C 49.69; H 3.71; N 23.88.

Method C

Preparation of 6-alkyl(cycloalkyl)-8-methylimidazo[1,5-d]-as-triazin-4(3H)-ones

The above compounds are prepared by Method A excepting that the mixture of 2-alkyl(cycloalkyl)-5-methylimidazole-4-carboxaldehyde methyl carbazone and o-dichlorobenzene is heated until a boiling point of 180° C. is obtained. The solvent is removed by evaporation and the residue recrystallized from the appropriate solvent.

The compounds prepared by Methods A, B and C, their melting points and analyses are listed in Table VI below.

TABLE VI

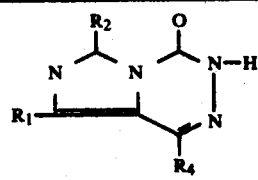

| | | | | | Analysis | |
|---|---|---|---|---|---|---|
| $R_1$ | $R_2$ | $R_4$ | Method | M.p.(°C.) | Calculated | Found |
| $CH_3$ | CH₃—⌬— | H | A | 169–171.5(d) | | |
| $CH_3$ | CH₃O—⌬— | H | A | 216–217(d) | C 60.93<br>H 4.72<br>N 21.86 | C 60.52<br>H 4.80<br>N 21.70 |
| $CH_3$ | Cl—⌬— | H | A | >240(d) | | |
| $CH_3$ | ⌬—CH₃ (ortho) | H | A | 185–191(d) | | |

TABLE VI-continued

Structure: imidazo-triazinone core with substituents R1, R2, R4

| R1 | R2 | R4 | Method | M.p.(°C.) | Calculated | Found |
|---|---|---|---|---|---|---|
| CH3 | naphthyl | H | A | 247–251(d) | | |
| Cl | (4-chlorophenyl) | H | B | 245–246(d) | C 47.00<br>H 2.15<br>N 19.93<br>Cl 25.23 | C 47.72<br>H 2.41<br>N 19.57<br>Cl 24.75 |
| H | phenyl | CH3 | A | 281–281.5 | | |
| CH3 | phenyl | CH3 | A | 207–212 | | |
| CH3 | $C_4H_9$— | H | C | 118–120 | C 58.23<br>H 6.84<br>N 27.17 | C 58.36<br>H 6.84<br>N 27.14 |
| H | $C_6H_{13}$— | H | C | 118–119 | C 61.51<br>H 7.74<br>N 23.91 | C 61.28<br>H 7.61<br>N 23.68 |
| H | cyclopropyl | H | C | 210.5–211.5 | C 56.83<br>H 5.30<br>N 29.46 | C 56.65<br>H 5.64<br>N 29.43 |
| H | cyclopentyl | H | C | 179–181 | | |
| H | cyclohexyl | H | C | 145–147 | C 64.94<br>H 7.78<br>N 21.15 | C 63.88<br>H 8.10<br>N 20.41 |

EXAMPLE 107

6-Phenyl-8-iodo-imidazo[1,5-d]-as-triazin-4(3H)-one

3-[1-(5-Iodo-2-phenyl-4-imidazolyl)ethylidene]-carbazic acid methyl ester (1.01 gm., 0.0027 mole) is dissolved in a mixture of o-dichlorobenzene (150 ml.) and methanol (15 ml.). The solution is heated to the boiling point and boiled for 20 minutes allowing solvent to distill off partially. The reaction mixture is chromatographed over a silica gel column and eluted with a hexane-ethyl acetate (2:1) mixture to yield the title product (0.63 gm., 0.0019 mole). Recrystallization from ethyl acetate-hexane yields the product as yellow needles, m.p. 176°–189° C.

EXAMPLE 108

6-(p-Anilino)-8-methyl-imidazo[1,5-d]-as-triazin-4(3H)-one

Catalytic reduction of 8-methyl-6-(p-nitrophenyl)-imidazo[1,5-d]-as-triazin-4(3H)-one, monohydrate (1.3 gm., 0.0048 mole) in dimethylformamide (50 ml.) with hydrogen in the presence of 10% Pd/C catalyst and at atmospheric pressure, followed by solvent removal in vacuo, affords the product (1.0 gm., 0.0043 mole). Crystallization from dimethylformamide-water yields a mustard-yellow solid, m.p. 252°–254° C.(d).

EXAMPLE 109

8-Bromo-6-(m-anilino)imidazo-[1,5-d]-as-triazin-4(3H)-one.

A mixture of 8-bromo-6-(m-nitrophenyl)imidazo[1,5-d]-as-triazin-4(3H)-one (2.0 gm., 0.00595 mole) and catalyst (Ru/C, 5%, 700 mg) are blanketed with nitrogen at atmospheric pressure and dimethylformamide (45 ml.) is added. The flask containing the above mixture is vigorously shaken while hydrogen is introduced and absorbed (399 ml., 0.01785 mole). The catalyst is then filtered and washed with dimethylformamide. The filtrate is evaporated in vacuo. The product is recrystallized from diethyl ether, m.p. 205° C.(d).

EXAMPLE 110

8-Bromo-6-(m-dimethylaminophenyl)-imidazo-[1,5-d]-as-triazin-4(3H)-one.

Sodium cyanoborohydride (1.2 gm., 0.019 mole) is added to a stirred solution of 8-bromo-6-(m-aminophenyl)imidazo-[1,5-d]-as-triazine-4(3H)-one, aqueous formaldehyde (5 ml., 37%) in acetonitrile (110 ml.). The reaction mixture is stirred for 15 minutes then acetic acid is added to adjust the pH of the reaction mixture to 7. The reaction mixture is stirred for 45 minutes while the pH of the mixture is maintained at 7 with acetic acid being added as needed. The solvent is then evaporated in vacuo, the residual oil is added to 2 N potassium hydroxide (150 ml.), and crystallizes. The product is washed with water, and recrystallized from acetone-water, m.p. 206° C.(d).

EXAMPLE 111

6-(m-Nitrophenyl-imidazo[1,5-d]-as-triazin-4(3H)-one

A mixture of 90% fuming nitric acid 0.4 ml.; d=1.5, 0.0086 mole) and sulfuric acid (10 ml) is added slowly at 5° C. to a solution of 6-phenyl-imidazo[1,5-d]-as-triazin-4(3H)-one (2.12 gm., 0.01 mole) in sulfuric acid (50 ml.). The mixture is stirred overnight (appr. 15–16 hours) at room temperature, and then poured over ice. The mixture is made slightly alkaline, stirred with ethyl acetate and is filtered. The isolated solid is recrystallized from aqueous dimethylformamide to yield 0.83 gm. of a buff-colored, fluffy solid (32%), m.p. 294°–296° C. (with violent decomposition).

Analysis calculated for $C_{11}H_7N_5O_3$: C 51.36; H 2.74; N 27.23; Found: C 51.28; H 2.85; N 27.17.

EXAMPLE 112

8-Bromo-6-(m-nitrophenyl)-imidazo[1,5-d]-as-triazin-4(3H)-one, compound with dimethylformamide.

A mixture of 90% fuming nitric acid (1.87 ml.; d=1.5, 0.04 mole) and sulfuric acid (10 ml.) is added slowly at 5° C. to a solution of 8-bromo-6-phenyl-imidazo[1,5-d]-as-triazin-4(3H)-one (5.82 gm., 0.02 mole) in sulfuric acid. The reaction mixture is stirred for 1 hour, poured over ice, the precipitated solid isolated by filtration and dried. A dark brown solid (6.58 gm., 98%) is obtained, m.p. 244°–246° C.(d). Recrystallization from aqueous dimethylformamide yields the title compound, a buff colored solid, m.p. 246°–248° C.(d).

Analysis calculated for $C_{11}H_6BrN_5O_3 \cdot C_3H_7NO$: C 41.09; H 3.20; N 20.54; Br 19.53; Found: C 40.99; H 3.15; N 20.34; Br 20.50.

EXAMPLE 113

8-Bromo-imidazo[1,5-d]-as-triazin-4(3H)-one.

A solution of bromine (8.0 gm., 0.05 mole) in acetic acid (10 ml.) is added to a mixture of imidazo[1,5-d]-as-triazin-4(3H)-one (6.8 gm., 0.05 mole) and acetic acid (500 ml.). The reaction mixture is stirred for 1 hour, poured into water and extracted with chloroform. The aqueous layer is separated, made slightly alkaline and extracted with ether. Evaporation of the chloroform and the ether layers yields 5.0 gm. of a solid (46.3%). This solid is recrystallized to afford the title product, a cream colored solid, m.p. 244°–245° C.(d).

Analysis calculated for $C_5H_3BrN_4O$: C 27.80; H 1.40; N 25.94; Br 37.00; Found: C 28.99; H 1.36; N 26.46; Br 35.91.

EXAMPLE 114

6,8-Dibromo-imidazo[1,5-d]-as-triazin-4(3H)-one

Bromine (1.5 ml., 0.03 mole) is added dropwise to a well stirred mixture of imidazo[1,5-d]-as-triazin-4(3H)-one (1.36 gm., 0.01 mole), sodium bicarbonate (2.52 gm., 0.03 mole) and water (25 ml.). The mixture is stirred for 4 hours and is then filtered. The isolated product is washed well with water and air-dried. The product (2.78 gm., 95%) is recrystallized from toluene-hexane (1:1) to yield a cream colored solid, m.p. 210°–212° C.

Analysis calculated for $C_5H_2Br_2N_4O$: C 20.44; H 0.69; N 19.10; Br 54.39; Found: C 19.16; H 0.88; N 18.80; Br 54.12.

EXAMPLE 115

8-Bromomethyl-6-phenyl-imidazo[1,5-d]-as-triazin-4(3H)-one.

A mixture of 8-methyl-6-phenylimidazo[1,5-d]-as-triazin-4(3H)-one (4.52 gm., 0.02 mole), N-bromosuccinimide (3.92 gm., 0.044 mole), benzoyl peroxide (0.24 gm., 0.002 mole) and carbon tetrachloride (200 ml.) is refluxed for 8 hours. The reaction mixture is cooled and filtered. The isolated product is washed with water and with methylene chloride. The product (2.1 gm., 34.4%) is recrystallized from nitromethane to yield pale yellow crystals, m.p. 254°–256° C.(d).

Analysis calculated for $C_{12}H_9BrN_4O$: C 47.24; H 2.97; N 18.48; Br 26.20; Found: C 47.50; H 3.21; N 18.48; Br 25.78.

Evaporation of the filtrate and washings, followed by recrystallization of the residue from nitromethane yields a second crop (14.8%) of the product.

EXAMPLE 116

Preparation of 3-Alkyl-8-methyl-6-phenylimidazo-as-[1,5-d]-triazin-4(3H)-ones.

Method A

Sodium methoxide (0.81 gm., 0.015 mole) is added to a solution of 8-methyl-6-phenylimidazo-as-[1,5-d]-triazin-4(3H)-one (3.39 gm., 0.015 mole), followed by the addition of the appropriate alkylating agent (i.e. methyl iodide, allyl bromide, propargyl bromide, benzyl chloride, dipropyl sulfate, and the like). The reaction mixture is then stirred at 20° C. for 16 hours, heated at 40° C. for 45 minutes, cooled and poured on a mixture of ice and dilute hydrochloric acid. The product is extracted from the above aqueous mixture with chloroform and isolated by evaporation of the chloroform layer. Purification is effected by crystallization (cyclohexane or cyclohexane-benzene), or by silica gel dry column chromatography in chloroform.

Method B 3,8-Dimethyl-6-phenylimidazo[1,5-d]-as-triazin-4(3H)-one.

Dimethylformamide dimethyl acetal (0.73 ml.; d=0.087, 0.005 mole) is added slowly to a slurry of 8-methyl-6-phenylimidazo[1,5-d]-as-triazin-4(3H)-one (1.13 gm., 0.005 mole) in benzene (25 ml.). The reaction mixture is stirred, refluxed for 24 hours, cooled and filtered. The filtrate is evaporated to yield 1.4 gm. (100%) product. Recrystallization from methyl cyclohexane yields yellow crystals, found to be identical (ir; nmr) to the product obtained by Method A.

Compounds prepared by the above procedures are listed in Table VII below.

TABLE VII

[Structure: imidazo-triazinone with phenyl, CH3, and N-R3 substituents]

| R3 | Method | m.p. (°C.) | Analysis Calculated | Found |
|---|---|---|---|---|
| CH3 | A or B | 144–146 | C 64.98<br>H 5.03<br>N 23.32 | C 65.09<br>H 5.11<br>N 23.45 |
| CH2=CH—CH2 | A | 134–134.5 | C 67.65<br>H 5.30<br>N 21.04 | C 67.70<br>H 5.25<br>N 21.21 |
| CH≡CH—CH2 | A | 192.5–193.5 | C 68.17<br>H 4.58<br>N 21.20 | C 67.70<br>H 4.56<br>N 21.17 |
| C3H7 | A | 144.5–145 | C 67.14<br>H 6.01<br>N 20.88 | C 67.15<br>H 6.19<br>N 20.96 |
| ⌬—CH2 | A | 143–144 | C 72.13<br>H 5.10<br>N 17.71 | C 17.71<br>H 5.24<br>N 17.42 |

EXAMPLE 117

3,8-Dimethyl-6-phenyl-imidazo[1,5-d]-as-triazine-4(3H)-thione.

8-Methyl-6-phenyl-imidazo[1,5-d]-as-triazine-43H)-thione (3.76 gm., 0.014 mole) is dissolved in aqueous sodium bicarbonate (125 ml., 6.7%). Dimethyl sulfate (1.85 gm., 0.0147 mole) is added at room temperature and the reaction mixture stirred overnight (appr. 15–16 hours). The precipitated solid is collected by filtration and washed thoroughly with water. The dried solid (3.84 gm.) is extracted with benzene. The benzene solution is evaporated to dryness, and the residual red solid obtained is extracted with hexane. Evaporation of the hexane solution yields a tan solid (0.25 gm.). Recrystallization of this tan solid from methanol yields pale yellow crystals, m.p. 194°–195° C.

Analysis calculated for $C_{13}H_{12}N_4S$: C 60.92; H 4.72; N 21.86; Found: C 60.31; H 4.90; N 21.34.

EXAMPLE 118

Preparation of m-Trifluoromethylphenyliminoethyl ester (hydrochloride).

A mixture of m-trifluoromethylbenzonitrile (100.0 g; 0.585 mole), ether (200 ml) and absolute ethanol (100 ml) is stirred, cooled to 0°–5° C. and anhydrous HCl gas bubbled in for 1.5 hours. The reaction mixture is then stored in the cold overnight. The mixture is then filtered, washed with ether and the white crystalline solid dried in vacuum at room temperature to yield 124.47 g of title product, m.p. 131°–132° C.

Analysis calculated for $C_{10}H_{11}NClF_3O$: C 47.35; H 4.37; N 5.52; Cl 13.98; F 22.47; Found: C 47.36; H 4.39; N 5.45; Cl 14.03; F 22.55.

EXAMPLE 119

Preparation of m-Trifluoromethylphenylamidine hydrochloride.

A mixture of m-trifluoromethylphenyliminoethyl ester hydrochloride (119 g) and absolute ethanol (595 ml) is stirred and ammonia gas bubbled in slowly at room temperature for 0.5 hours, then let stand overnight. Then the addition of ammonia gas is resumed at 30° C. until solution occurs. Ether is added, the precipitated material filtered, washed with ether and dried to afford 119.48 g of title product, m.p. 181°–182° C.

Analysis calculated for $C_8H_8N_2ClF_3$: C 42.78; H 3.59; N 12.47; Cl 15.78; F 25.37; Found: C 42.40; H 3.71; N 12.36; Cl 16.34; F 25.43.

EXAMPLE 120

Preparation of cis and trans 4,5-dimethyl-2-(α,α,α-trifluoro-m-tolyl)-2-imidazoline-4,5-diol hydrochloride 2,3-Butanedione (49.1 ml) is added dropwise over 30 minutes to a warm (45° C.) solution of m-trifluoromethylphenylamidine hydrochloride (110.48 g; 0.53 mole) in water (480 ml). The reaction mixture is stirred overnight at room temperature, and then stripped at 40° C. The isolated crude solid contains about 77.3 g of amidine. The amidine, water (100 ml) and 2,3-butanedione (31 ml) are mixed and reacted in an ice bath for 2 hours. The mixture is then filtered, washed with hexane to afford 55.96 g of title product. Total yield: 119.0 g.

Analysis calculated for $C_{12}H_{14}N_2ClF_3O_2$: C 46.39; H 4.54; N 9.02; Cl 11.41; F 18.34; Found: C 45.03; H 4.78; N 9.65; Cl 12.57; F 18.07.

EXAMPLE 121

Preparation of 5-Methyl-2-(α,α,α-trifluoro-m-tolyl)-4-imidazolemethanol.

A mixture of 4,5-dimethyl-2-(α,α,α-trifluoro-m-tolyl)-2-imidazoline-4,5-diol hydrochloride (116 g; 0.418 mole) and 3 N hydrochloric acid (1785 ml) is heated at 90° C. for 2.5 hours. The reaction mixture is then cooled in an ice bath with stirring for 45 minutes, and then filtered. The isolated solid (8.0 g, m.p. 101.5°–100° C.) is different from the title product by IR and NMR.

The filtrate is concentrated at room temperature overnight to afford 36.73 g of title product, m.p. 183° C. with decomposition. Further evaporation of the filtrate yields additional 24.0 g of product.

Analysis calculated for $C_{12}H_{12}N_2ClF_3O$: C 49.24; H 4.13; N 9.57; Cl 12.11; F 19.47; Found: C 48.94; H 4.16; N 9.55; Cl 12.20; F 19.78.

EXAMPLE 122

Preparation of 5-methyl-2-(α,α,α-trifluoro-m-tolyl)imidazole-4-carboxaldehyde.

A mixture of 5-methyl-2-(α,α,α-trifluoro-m-tolyl)-4-imidazolemethanol (30.0 g), manganese dioxide (200 g) and chloroform (1000 ml) is stirred at room temperature for 7 hours, and then filtered, and the solution allowed to stand over the weekend. Ethyl acetate is added to dissolve precipitated material and the solution is filtered. The solution is then evaporated to dryness in vacuo to afford 26.34 g solid, m.p. 179.5°–180° C.

EXAMPLE 123

Preparation of 3-{[5-methyl-2-(α,α,α-trifluoro-m-tolyl)-4-imidazolyl]-methylene}carbazic acid methyl ester A mixture of 5-methyl-2-(α,α,α-trifluoro-m-tolyl)imidazole-4-carboxaldehyde (20.0 g, 0.0787 mole), methanol (500 ml), methyl carbazate (7.8 g) and glacial acetic acid (0.5 ml) is refluxed overnight. The solution is then concentrated to afford 23.14 g of title product. A sample is recrystallized from methanol-acetone, m.p. 251°–251.5° C.

Analysis calculated for $C_{14}H_{13}N_4F_3O_2$: C 51.53; H 4.02; N 17.17; F 17.47; Found: C 51.58; H 4.05; N 17.11 F 17.27.

EXAMPLE 124

Preparation of 8-Methyl-6-(α,α,α-trifluoro-m-tolyl)imidazo[1,5-d]-as-triazin-4(3H)-one 3-{[5-Methyl-2-(α,α,α-trifluoro-m-tolyl)-4-imidazolyl]-methylene}carbazic acid methyl ester (3.0 g) is added rapidly to diphenyl ether (50 ml) preheated to 297° C., and the mixture is then kept at 297° for 15 minutes. The mixture is rapidly cooled to room temperature, hexane (50 ml) is added and the mixture filtered to yield 4.2 g yellow solid. This material is chromatographed on a silica gel column using a hexane-ethyl acetate mixture as eluent. The fractions found to be identical by TLC are combined to afford 1.86 g of the title product, m.p. 194°–194.5° C.

Analysis calculated for $C_{13}H_9N_4F_3O$: C 53.07; H 3.08; N 19.04; F 19.37; Found: C 52.97; H 3.04; N 18.90; F 19.16.

EXAMPLE 125

Preemergence Herbicidal Activity

The preemergence herbicidal activity of the compounds of the present invention is exemplified by the following tests in which the seeds or propagating organs of a variety of monocotyledonous and dicotyledonous plants are separately mixed with potting soil and planted on top of approximately 2.5 cm. of soil in separate cups. After planting, the cups are sprayed with the selected aqueous acetone solution containing test compound is sufficient quantity to provide the equivalent of about 0.07 kg to 11.2 kg per hectare of test compound per cup. The treated cups are then placed on greenhouse benches, watered and cared for in accordance with conventional greenhouse procedures. Three to five weeks after treatment, the tests are terminated and each cup is examined and rated according to the rating system provided below. The data obtained are reported in Table VIII below.

| Rating System: | Difference in Growth from the Check* |
|---|---|
| 0 - No effect | 0 |
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth; that is, a definite physiological malformation but with an over-all effect less than a 5 on the rating scale. | |

*Based on visual determination of stand, size, vigor, chlorosis, growth malformation and over-all plant appearance.

Plant Abbreviations

SE—Sesbania (Sesbania exaltata)
LA—Lambsquarters (Chenopodium album)
MU—Mustard (Brassica kaber)
PI—Pigweed (Amaranthus retroflexus)
RW—Ragweed (Ambrosia artemisiifolia)
MG—Morningglory (Ipomoea purpurea)
BA—Barnyardgrass (Echinochloa crusgalli)
CR—Crabgrass (Digitaria sanguinalis)
FO—Green Foxtail (Setaria viridis)
WO—Wild Oats (Avena fatua)
TW—Teaweed (Sida spinosa)
VL—Velvetleaf (Abutilon theophrasti)
JW—Jimsonweed (Datura stramonium L.)

TABLE VIII

Evaluation of the preemergence herbicidal activity of imidazo-as-triazinones and triazinethions for the control of mono- and dicotyledonous weeds.

| Compound | Rate: kg/ha | SE | LA | MU | PI | RW | MG | TW | VL | BA | CR | FO | WO | JW |
|---|---|---|---|---|---|---|---|---|---|---|---|---|---|---|
| 8-Methyl-imidazo[1,5-d]-as-triaine-4(3H)-thione | 11.2 | 9 | | 9 | 9 | 7 | 2 | 9 | 9 | 7 | 6 | 7 | 0 | |
| | 4.48 | 5 | | 8 | 8 | 0 | 3 | 9 | 9 | 5 | 7 | 3 | | |
| | 1.12 | 0 | | 0 | 0 | 0 | 0 | 0 | 0 | 0 | 0 | 0 | | |
| 6-Phenyl-imidazo[1,5-d]-as-triazine-4(3H)-thione | 11.2 | 8 | | 9 | 9 | 8 | 0 | 9 | 9 | 5 | 7 | 7 | 0 | |
| | 4.48 | 3 | | 9 | 1 | 7 | 0 | 3 | 0 | 3 | 6 | 1 | | |
| | 1.12 | 1 | | 0 | 0 | 0 | 0 | 0 | 0 | 0 | 0 | 0 | | |
| 6-n-propyl-imidazo[1,5-d]-as-triazine-4(3H)-thione | 11.2 | 0 | | 8 | 9 | 0 | 4 | 3 | 0 | 2 | 6 | 8 | 1 | |
| | 4.48 | 5 | | 1 | 2 | | 0 | 0 | 0 | 3 | 2 | 3 | | |
| | 1.12 | 0 | | 0 | 0 | 0 | 0 | 0 | 0 | 0 | 0 | 0 | | |
| 8-methyl-6-phenyl-imidazo[1,2-d]-as-triazine-4(3H)-thione | 11.2 | 9 | | 9 | 9 | 9 | 9 | 9 | 9 | 9 | 9 | 9 | 9 | |
| | 4.48 | 9 | | 9 | 9 | 9 | 8 | 5 | 9 | 9 | 9 | 9 | 6 | |
| | 1.12 | 9 | | 9 | 8 | 8 | 0 | 0 | 2 | 7 | 6 | 7 | 6 | |
| | 0.56 | 7 | | 8 | 3 | 0 | 0 | 0 | 0 | 6 | 5 | 3 | 1 | |
| | 0.28 | 0 | | 5 | 0 | | 0 | 0 | 0 | 3 | 0 | 0 | 0 | |
| 3,8-Dimethyl-6-phenyl-imidazo-[1,5-d]-as-triazin-4(3H)-one | 11.2 | 9 | | 9 | 9 | 9 | 9 | 9 | 9 | 8 | 9 | 9 | 8 | |
| | 2.24 | | 8 | | 9 | 5 | 9 | 9 | 9 | 3 | 7 | 7 | 8 | 8 |
| | 1.12 | 8 | | | 9 | 0 | 9 | 8 | 5 | 0 | 2 | 0 | 0 | 3 |
| | 0.56 | 0 | 7 | | 0 | 8 | 7 | 0 | 0 | 0 | 0 | 0 | 3 | |
| | 0.28 | 0 | | | 8 | 0 | 5 | 0 | 0 | 0 | 0 | 0 | 0 | 0 |
| 8-methyl-6-phenyl-3-n-propyl-imidazo[1,5-d]-as-triazin-4(3H)-one | 11.2 | 9 | | 8 | 9 | 0 | 0 | 9 | 2 | 8 | 9 | 9 | 8 | |
| | 2.24 | | 8 | | 9 | 0 | 0 | 9 | 0 | 3 | 5 | 3 | 1 | 9 |
| | 1.12 | | 0 | | 2 | 0 | 0 | 2 | 0 | 0 | 1 | 0 | 0 | 3 |
| 8-methyl-3-propynyl-6-phenyl-imidazo[1,5-d]-as-triazin-4(3H)-one | 11.2 | 9 | | 9 | 9 | 0 | 9 | 9 | 8 | 7 | 9 | 9 | 7 | |
| | 2.24 | | 8 | | 9 | 3 | 9 | 9 | 3 | 3 | 8 | 5 | 0 | 7 |
| | 1.12 | | 2 | | 9 | 0 | 0 | 9 | 0 | 2 | 7 | 2 | 0 | 7 |
| | 0.56 | | 0 | | 9 | 0 | 0 | 9 | 0 | 0 | 0 | 0 | 0 | 0 |
| 3-alkyl-8-methyl-6-phenyl-imidazo- | 11.2 | 0 | | 7 | 8 | 6 | 7 | 9 | 8 | 6 | 9 | 9 | 3 | |
| | 2.24 | 9 | | | 9 | 2 | 0 | 0 | 0 | 2 | 9 | 5 | 2 | |

TABLE VIII-continued
Evaluation of the preemergence herbicidal activity of imidazo-as-triazinones and triazinethions for the control of mono- and dicotyledonous weeds.

| Compound | Rate: kg/ha | SE | LA | MU | PI | RW | MG | TW | VL | BA | CR | FO | WO | JW |
|---|---|---|---|---|---|---|---|---|---|---|---|---|---|---|
| [1,5-d]-as-triazin-4(3H)-one | 1.12 | | O | | 3 | 0 | 0 | 0 | 0 | 0 | 0 | 0 | 0 | |
| | 11.2 | 9 | | 9 | 8 | 8 | 9 | 9 | 9 | 8 | 9 | 9 | 7 | |
| 8-Bromomethyl-6-phenyl-imidazo-[1,5-d]-as-triazin-4(3H)-one | 2.24 | | 8 | | 2 | 1 | 9 | 0 | 0 | 5 | 5 | 3 | 8 | 9 |
| | 1.12 | | 2 | | 0 | 0 | 0 | 0 | 0 | 0 | 2 | 0 | 0 | 0 |
| | 11.2 | 9 | | 9 | 9 | 7 | 9 | 9 | 9 | 7 | 9 | 9 | 6 | |
| 8-Bromo-6-(m-nitrophenyl)imidazo-[1,5-d]-as-triazin-4(3H)-one | 2.24 | | 9 | | 9 | 2 | 9 | 0 | 0 | 6 | 8 | 5 | 7 | 2 |
| | 1.12 | | 9 | | 8 | 0 | 0 | 0 | 0 | 0 | 6 | 0 | 0 | 0 |
| | 11.2 | 9 | | 9 | 9 | 9 | 9 | 9 | 9 | 9 | 9 | 9 | 7 | |
| | 4.48 | 9 | | 9 | 9 | 9 | 9 | 9 | 9 | 7 | 9 | 9 | 9 | |
| 6-phenyl-imidazo[1,5-d]-as-triazin-4(3H)-one | 1.12 | 8 | | 9 | 8 | 9 | 8 | 9 | 9 | 6 | 7 | 6 | 7 | |
| | 0.56 | 6 | | 9 | 0 | 6 | 1 | 5 | 2 | 2 | 3 | 1 | 3 | |
| | 0.28 | 1 | | 1 | 0 | 1 | 1 | 0 | 0 | 1 | 0 | 0 | 1 | |
| | 11.2 | 9 | | 9 | 9 | 9 | 9 | 9 | 9 | 9 | 9 | 9 | 8 | |
| | 4.48 | 9 | | 9 | 9 | 9 | 9 | 9 | 9 | 9 | 9 | 9 | 9 | |
| | 2.24 | | 9* | | 9* | 9* | 9* | 9* | 9* | 9* | 9* | 9* | 9* | 9* |
| | 1.12 | 9* | 9* | 9* | 9* | 9* | 9* | 9* | 9* | 9* | 9* | 9* | 9* | 9* |
| 8-methyl-6-phenyl-imidazo[1,5-d]-as-triazin-4(3H)-one | 0.56 | 9* | 9* | 9* | 9* | 9* | 9* | 9* | 9* | 9* | 9* | 8.9* | 8.7* | 8.8* |
| | 0.28 | 9* | 9* | 9* | 8.9* | 8.6* | 8* | 8.4* | 8.5* | 8.7* | 8.7* | 8.1* | 8.6* | 8.6* |
| | 0.14 | 9* | 6.7* | 9* | 7.6* | 6.8* | 3.1* | 4.7* | 5.8* | 7.7* | 7.6* | 6.7* | 7.3* | 8.4* |
| | 0.07 | 3.5* | 4.2* | 4* | 2.8* | 4.5* | 1.3* | 0* | 1.7* | 5* | 4.5* | 2.8* | 3.8* | 4.4* |
| | 0.035 | 0 | 0 | 0 | 0* | 0* | 0* | 0* | 0* | 1* | 1* | 0* | 0* | 0 |
| | 11.2 | 7 | | 8 | 8 | 7 | 7 | 7 | 8 | 7 | 7 | 8 | 6 | |
| 6-n-propyl-imidazo[1,5-d]-as-triazin-4(3H)-one | 4.48 | 6 | | 9 | 8 | 3 | 6 | 7 | 6 | 5 | 6 | 5 | | |
| | 1.12 | 3 | | 7 | 0 | 0 | 0 | 0 | 0 | 2 | 2 | 0 | | |
| | 0.56 | 0 | | 0 | 0 | 0 | 0 | 0 | 0 | 0 | 0 | 0 | | |
| 6,8-Dimethyl-imidazo[1,5-d]-as-triazin-4(3H)-one | 11.2 | 7 | | 7 | 8 | 1 | 7 | 5 | 5 | 7 | 6 | 7 | 6 | |
| | 11.2 | 8 | | 9 | 8 | 6 | 7 | 8 | 6 | 7 | 7 | 8 | 6 | |
| 6-t-butyl-imidazo[1,5-d]-as-triazin-4(3H)-one | 4.48 | 5 | | 3 | 3 | 2 | 5 | 2 | 2 | 2 | 0 | 3 | | |
| | 1.12 | 3 | | 1 | 2 | 0 | 2 | 0 | 0 | 1 | 0 | 0 | | |
| | 5.6 | 8 | | 9 | 9 | 9 | 9 | 9 | 9 | 9 | 9 | 9 | 9 | |
| | 1.12 | 9 | | 9 | 9 | 9 | 9 | 9 | 9 | 9 | 9 | 9 | 9 | |
| 8-bromo-6-phenyl-imidazo[1,5-d]-as-triazin-4(3H)-one | 0.56 | 9 | | 9 | 9 | 9 | 9 | 9 | 9 | 9 | 9 | 9 | 9 | |
| | 0.28 | 9 | | 9 | 9 | 9 | 5 | 9 | 9 | 9 | 9 | 9 | 9 | |
| | 0.14 | 9 | | 9 | 9 | 9 | 0 | 8 | 8 | 9 | 9 | 9 | 6 | |
| | 11.2 | 9 | | 9 | 9 | 9 | 9 | 9 | 9 | 9 | 9 | 9 | 9 | |
| | 1.12 | 9 | | 9 | 9 | 9 | 9 | 9 | 9 | 9 | 9 | 9 | 9 | |
| 8-Chloro-6-phenyl-imidazo[1,5-d]-is-triazin-4(3H)-one | 0.56 | 9 | | 9 | 9 | 9 | 9 | 9 | 9 | 9 | 9 | 9 | 9 | |
| | 0.28 | 9 | | 9 | 9 | 9 | 8 | 9 | 9 | 9 | 9 | 9 | 9 | |
| | 0.14 | 9 | | 9 | 9 | 8 | 0 | 8 | 9 | 9 | 9 | 9 | 7 | |
| | 11.2 | 7 | | 6 | 7 | 6 | 9 | 2 | 2 | 7 | 2 | 6 | 4 | |
| 8-Methyl-imidazo[1,5-d]-as-triazin-4(3H)-one | 4.48 | 2 | | 3 | 8 | 0 | 0 | 0 | 0 | 2 | 2 | 2 | | |
| | 1.12 | 0 | | 0 | 0 | 0 | 0 | 0 | 0 | 0 | 0 | 0 | | |
| | 11.2 | 8 | | 8 | 9 | 8 | 9 | 9 | 9 | 9 | 9 | 9 | 9 | |
| 6-t-butyl-8-methyl-imidazo[1,5-d]-as-triazin-4(3H)-one | 4.48 | 9 | | 9 | 9 | 9 | 9 | 9 | 5 | 9 | 9 | 9 | 8 | |
| | 1.12 | 8 | | 7 | 5 | 6 | 2 | 2 | 0 | 6 | 5 | 3 | 7 | |
| | 0.56 | 2 | | 2 | 2 | 1 | 0 | 0 | 0 | 5 | 3 | 0 | 5 | |
| | 11.2 | 9 | | 9 | 9 | 9 | 9 | 9 | 9 | 9 | 9 | 9 | 8 | |
| | 4.48 | 9 | | 9 | 9 | 9 | 9 | 9 | 9 | 9 | 9 | 9 | 9 | |
| 8-Methyl-6-n-propyl-imidazo-[1,5-d]-as-triazin-4(3H)-one | 1.12 | 8 | | 9 | 9 | 9 | 3 | 0 | 1 | 8 | 9 | 9 | 6 | |
| | 0.56 | 1 | | 5 | 7 | 9 | 0 | 0 | 0 | 7 | 7 | 7 | 5 | |
| | 0.28 | 0 | | 0 | 0 | 0 | 0 | 0 | 0 | 0 | 2 | 0 | 0 | |
| | 11.2 | 8 | | 9 | 9 | 9 | 5 | 2 | 9 | 7 | 8 | 9 | 6 | |
| 8-Methyl-6-n-propyl-8-imidazo-[1,5-d]-as-triazine-4(3H)-one | 4.46 | 5 | | 9 | 9 | 9 | 1 | 8 | 9 | 9 | 9 | 9 | | |
| | 1.12 | 0 | | 0 | 0 | 2 | 0 | 0 | 2 | 6 | 8 | 2 | | |
| | 0.56 | 0 | | 0 | 0 | 0 | 0 | 0 | 0 | 0 | 0 | 0 | | |
| | 11.2 | 9 | | 9 | 9 | 9 | 9 | 9 | 9 | 9 | 9 | 9 | 9 | |
| 8-Chloro-6-(p-chlorophenyl)-imidazo[1,5-d]-as-triazin-4(3H)-one | 1.12 | | 9 | | 9 | 6 | 0 | 6 | 8 | 5 | 8 | 6 | 3 | 8 |
| | 0.56 | | 8 | | 9 | 5 | 0 | 2 | 0 | 3 | 5 | 0 | 0 | 7 |
| | 0.28 | | 0 | | 8 | 0 | 0 | 0 | 0 | 0 | 0 | 0 | 0 | 0 |
| 8-bromo-imidazo[1,5-d]-as-triazin-4(3H)-one | 11.2 | 6 | | 9 | 9 | 0 | 6 | 8 | 8 | 4 | 7 | 7 | 5 | |
| | 2.24 | | 0 | | 8 | 0 | 0 | 0 | 2 | 0 | 2 | 0 | 0 | 0 |
| | 11.2 | 9 | | 9 | 9 | 9 | 9 | 9 | 9 | 9 | 9 | 9 | 9 | |
| 6-(p-methoxyphenyl)-8-methyl-imidazo[1,5-d]-as-triazin-4(3H)-one | 2.24 | | 9 | | 8 | 9 | 6 | 8 | 9 | 8 | 9 | 8 | 6 | 9 |
| | 1.12 | | 5 | | 3 | 7 | 2 | 0 | 2 | 7 | 8 | 8 | 1 | 8 |
| | 0.56 | | 2 | | 0 | 2 | 0 | 0 | 0 | 0 | 7 | 6 | 5 | 0 | 0 |
| | 11.2 | 0* | | 8* | 9* | 0* | 9* | 5* | 5* | 0* | 7* | 2* | 0* | |
| 3,8-dimethyl-6-phenyl-imidazo-[1,5-d]-as-triazine-4(3H)-thione | 1.12 | | 2 | | 6 | 0 | 0 | 3 | 6 | 0 | 2 | 2 | 0 | 5 |
| | 0.56 | | 0 | | 0 | 0 | 0 | | 0 | 0 | 0 | 0 | 0 | 0 |
| | 11.2 | 9* | | 9* | 9* | 9* | 9* | 9* | 9* | 9* | 9* | 9* | | |
| 8-methyl-6-(p-tolyl)-imidazo-[1,5-d]-as-triazin-4(3H)-one | 2.24 | | 9 | | 9 | 9 | 9 | 8 | 9 | 9 | 9 | 9 | 9 | 9 |
| | 1.12 | | 7 | | 2 | 2 | 0 | 0 | 2 | 7 | 7 | 7 | 5 | 5 |
| | 0.56 | | 0 | | 0 | 0 | 0 | 0 | 0 | 3 | 3 | 3 | 5 | 0 |
| | 11.2 | 9 | | 9 | 9 | 9 | 9 | 9 | 9 | 9 | 9 | 9 | 9 | |
| | 2.24 | | 9 | | 9 | 9 | 9 | 9 | 9 | 9 | 9 | 9 | 9 | 9 |
| 6-cyclohexyl-8-methyl-imidazo-[1,5-d]-as-triazin-4(3H)-one | 1.12 | | 9 | | 7 | 9 | 9 | 8 | 9 | 9 | 9 | 9 | 9 | 9 |
| | 0.56 | | 9 | | 3 | 8 | 6 | 2 | 9 | 9 | 9 | 9 | 9 | 9 |
| | 0.28 | | 7 | | 0 | 5 | 0 | 0 | 0 | 8 | 6 | 5 | 8 | 9 |

TABLE VIII-continued

Evaluation of the preemergence herbicidal activity of imidazo-as-triazinones and triazinethions for the control of mono- and dicotyledonous weeds.

| Compound | Rate: kg/ha | SE | LA | MU | PI | RW | MG | TW | VL | BA | CR | FO | WO | JW |
|---|---|---|---|---|---|---|---|---|---|---|---|---|---|---|
| ⊕ | 0.14 | | 3 | | 0 | 0 | 0 | 0 | 0 | 2 | 2 | 0 | 3 | 5 |
| | 11.2 | 9 | | 9 | 9 | 9 | 9 | 9 | 9 | 9 | 9 | 8 | 7 | |
| | 2.24 | | 9 | | 9 | 9 | 9 | 9 | 9 | 9 | 5 | 5 | 9 | 9 |
| 6-n-hexyl-8-methyl-imidazo-[1,5-d]-as-triazin-4(3H)-one | 1.12 | | 5 | | 5 | 3 | 9 | 0 | 5 | 5 | 0 | 0 | 3 | 2 |
| | 0.56 | | 3 | | 2 | 1 | 3 | 0 | 0 | 2 | 0 | 0 | 2 | 0 |
| | 0.28 | | 0 | | 0 | 0 | 0 | 0 | 0 | 0 | 0 | 0 | 2 | 0 |
| | 11.2 | 9 | | 9 | 9 | 9 | 9 | 9 | 9 | 9 | 9 | 9 | 9 | |
| | 2.24 | | 9 | | 9 | 9 | 9 | 9 | 9 | 9 | 9 | 9 | 9 | 9 |
| 8-methyl-6-(m-tolyl)-imidazo-[1,5-d]-as-triazin-4(3H)-one | 1.12 | | 9 | | 9 | 9 | 9 | 9 | 9 | 9 | 9 | 9 | 9 | 9 |
| | 0.56 | | 9 | | 9 | 9 | 9 | 9 | 9 | 9 | 9 | 9 | 9 | 9 |
| | 0.28 | | 9 | | 0 | 9 | 9 | 2 | 2 | 9 | 9 | 9 | 9 | 9 |
| | 0.14 | | 7 | | 0 | 5 | 0 | 0 | 0 | 2 | 3 | 0 | 3 | 0 |
| 8-methyl-6-(o-tolyl)-imidazo-[1,5-d]-as-triazin-4(3H)-one | 11.2 | 9 | | 9 | 7 | 9 | 9 | 8 | 8 | 7 | 7 | 6 | 8 | |
| | 2.24 | | 0 | | 0 | 0 | 0 | 0 | 0 | 0 | 0 | 0 | 3 | 0 |
| 1-methyl-6-phenyl-imidazo[1,5-d]-as-triazin-4(3H)-one | 11.2 | 1 | | 2 | 0 | 0 | 2 | 7 | 8 | 0 | 8 | 0 | 0 | |
| | 1.12 | | 2 | | 0 | 2 | 0 | 0 | 2 | 0 | 0 | 0 | 2 | 1 |
| | 1.12 | | 9 | | 9 | 9 | 9 | 9 | 9 | 9 | 9 | 9 | 9 | 9 |
| 8-iodo-6-phenyl-imidazo[1,5-d]-as-triazin-4(3H)-one | 0.56 | | 9 | | 9 | 9 | 3 | 9 | 8 | 9 | 9 | 8 | 8 | 9 |
| | 0.28 | | 9 | | 9 | 9 | 0 | 3 | 5 | 5 | 5 | 5 | 7 | 7 |
| | 0.14 | | 3 | | 9 | 7 | 0 | 1 | 0 | 3 | 3 | 3 | 0 | 8 |
| 8-methyl-6-(α,α,α-trifluoro-m-(tolyl)-imidazo[1,5-d]-as-triazin-4(3H)-one | 1.12 | | 9 | | 7 | 9 | 9 | 9 | 9 | 9 | | 9 | 9 | 9 |
| | 0.56 | | 9 | | 8 | 8 | 8 | 2 | 3 | 9 | | 8 | 8 | 9 |
| | 0.28 | | 9 | | 2 | 3 | 2 | 1 | 1 | 3 | | 2 | 3 | 7 |

*=Average of two or more replicates

EXAMPLE 126

Postemergence Herbicidal Activity

The postemergence herbicidal activity of the compounds of the present invention is demonstrated by the following tests, wherein a variety of monocotyledonous, and dicotyledonous plants are treated with test compounds dispersed in aqueous acetone mixtures. In the tests, seedling plants are grown in separate cups for about 2 weeks. The test compounds are dispersed in 50/50 acetone/water mixtures containing 0.5% TWEEN® 20, a polyoxyethylene sorbitan monolaurate surfactant of Atlas Chemical Industries, in sufficient quantity to provide the equivalent of about 0.07 kg to 11.2 kg per hectare of active compound when applied to the plants through a spray nozzle operating at 2.81 kg/cm$^2$ pressure for a predetermined time. After spraying, the plants are placed on greenhouse benches and are cared for in the usual manner, commensurate with conventional greenhouse practices. Two weeks after treatment, the seedling plants are examined and rated according to the rating system set forth in Example 118. The data obtained are reported in Table IX below.

TABLE IX

Evaluation of the postemergence herbicidal activity of imidazo-as-triozinones and triazinethiones for the control of mono- and dicotyledonous weeds.

| Compound | Rate: kg/ha | SE | LA | MU | PI | RW | MG | TW | VL | BA | CR | FO | WO | JW |
|---|---|---|---|---|---|---|---|---|---|---|---|---|---|---|
| | 11.2 | 9 | | 9 | 9 | 9 | 9 | 9 | 9 | 9 | 9 | 9 | 9 | |
| | 4.48 | 9* | | 9* | 9* | 9* | 9* | 9* | 9* | 9* | 9* | 9* | 8.5* | |
| 8-methyl-6-phenyl-imidazo[1,5-d]-as-triazine-4(3H)-thione | 2.24 | 9 | | 9 | 6 | 7 | 6 | | | 3 | 3 | 3 | | 9 |
| | 1.12 | 9* | | 9* | 7* | 6* | 9* | 3 | 3 | 3* | 2* | 5* | 1 | 9 |
| | 0.56 | 9* | | 8.5* | 5.5* | 6* | 7* | 1 | 1 | 1 | 1.5* | 4.5* | 0 | 9 |
| | 0.28 | 7.5* | | 7.5* | 4* | 4.5* | 4.5* | 1 | 1 | 1* | 0.5* | 1.5* | 0* | 6 |
| | 11.2 | 9 | | 9 | 9 | 9 | 9 | 9 | 9 | 9 | 9 | 9 | | |
| | 4.48 | 9 | | 9 | 9 | 9 | 9 | 9 | 9 | 9 | 9 | 9 | | 9* |
| 8-methyl-6-phenyl-imidazo[1,5-d]-as-triazin-4(3H)-one | 2.24 | | 9* | | 9* | 8.7* | 9* | 5.7* | 9* | 7.3* | 4.4* | 7* | 5.7* | 9* |
| | 1.12 | 9 | 8.7* | 9 | 9* | 8.7* | 9* | 3.7* | 8* | 3.5* | 3* | 3.2* | 4.2* | 8.3* |
| | 0.56 | 3 | 6.3* | 9 | 8.2* | 5.7* | 7.2* | 2.5 | 7* | 0.5* | 0.5* | 0.5* | 1.7* | 7* |
| | 0.28 | 2 | 3.3* | 9 | 7.5* | 1.7* | 4* | 0.5* | 4.5* | 0* | 0* | 0.2* | .1* | 2.3* |
| | 0.14 | | 2* | | 9* | 0* | 2* | ·0* | 3.3* | 0* | 0* | 0* | 0* | 0* |
| 8-bromo-6-phenyl-imidazo[1,5-d]-as-triazin-4(3H)-one | 5.6 | 9 | | 9 | 9 | 9 | 9 | 9 | 9 | 9 | 9 | 9 | 9 | |
| 8-chloro-6-phenyl-imidazo[1,5-d]-as-triazin-4(3H)-one | 11.2 | 9 | | 9 | 9 | 9 | 9 | 9 | 9 | 9 | 9 | 9 | 9 | |
| | 11.2 | 8 | | 9 | 9 | 9 | 5 | 6 | 7 | 5 | 7 | 7 | 7 | |
| 6-t-butyl-8-methyl-imidazo[1,5-d]-as-triazin-4(3H)-one | 4.48 | 9 | | 9 | 9 | 3 | 9 | 3 | 1 | 5 | 5 | 6 | 8 | |
| | 1.12 | 2 | | 8 | 8 | 2 | 9 | 5 | 0 | 3 | 3 | 3 | 2 | |
| | 0.56 | 1 | | 0 | 0 | 0 | 8 | 1 | 0 | 2 | 1 | 2 | 1 | |
| | 11.2 | 9 | | 9 | 9 | 9 | 9 | 8 | 9 | 7 | 5 | 6 | 9 | |
| | 4.48 | 9 | | 9 | 9 | 9 | 9 | 9 | 9 | 7 | 9 | 9 | 9 | |
| 8-methyl-6-n-propyl-imidazo[1,5-d]-as-triazin-4(3H)-one | 1.12 | 9 | | 9 | 9 | 9 | 9 | 5 | 6 | 6 | 7 | 8 | 6 | |
| | 0.56 | 9 | | 9 | .9 | 3 | 9 | 5 | 2 | 0 | 0 | 3 | 2 | |
| | 0.28 | 0 | | 0 | 9 | 0 | 3 | 0 | 0 | 0 | | 2 | 0 | |
| | 11.2 | 9 | | 9 | 9 | 9 | 8 | 9 | 9 | 8 | 9 | 9 | 9 | |
| | 4.48 | 9 | | 9 | 9 | 9 | 9 | 5 | .1 | 9 | 9 | 9 | 8 | |
| 8-methyl-6-n-propyl-imidazo[1,5-d]-as-triazine-4(3H)-thione | 1.12 | 9 | | 9 | 9 | 9 | 9 | 5 | 2 | 6 | 9 | 9 | 6 | |
| | 0.56 | 9 | | 9 | 9 | 0 | 9 | 2 | 1 | 1 | 1 | 9 | 2 | |
| | 0.28 | 5 | | 9 | 8 | 0 | 1 | 0 | ·0 | 0 | 0 | 9 | 1 | |

TABLE IX-continued
Evaluation of the postemergence herbicidal activity of imidazo-as-triozinones and triazinethiones for the control of mono- and dicotyledonous weeds.

| Compound | Rate: kg/ha | SE | LA | MU | PI | RW | MG | TW | VL | BA | CR | FO | WO | JW |
|---|---|---|---|---|---|---|---|---|---|---|---|---|---|---|
| 8-Chloro-6-(p-chlorophenyl)-imidazo[1,5-d]-as-triazin-4(3H)-one | 11.2 | 9 | | 9 | 1 | 9 | 9 | 9 | 9 | 9 | 9 | 9 | 8 | |
| | 2.24 | | 3 | | 9 | 0 | 7 | 0 | 2 | 0 | 0 | 2 | 2 | 8 |
| | 1.12 | | 3 | | 7 | 0 | 9 | 0 | 0 | 0 | 0 | 0 | 0 | 8 |
| | 0.56 | | 0 | | 3 | 0 | 0 | 0 | 0 | 0 | 0 | 0 | 0 | 7 |
| 6-(p-methoxyphenyl)-8-methyl-imidazo[1,5-d]-as-triazin-4(3H)-one | 11.2 | 9 | | 8 | 0 | 5 | 8 | 8 | 5 | 7 | 5 | 3 | 7 | |
| | 2.24 | | 9 | | 5 | 8 | 2 | 0 | 0 | 0 | 0 | 0 | 2 | 0 |
| | 1.12 | | 0 | | 0 | 0 | | 0 | 0 | 0 | | | | |
| 8-methyl-6-(p-tolyl)-imidazo-[1,5-d]-as-triazin-4(3H)-one | 11.2 | 9 | | 9 | 9 | 9 | 8 | 9 | 6 | 9 | 6 | 9 | 8 | |
| | 11.2 | 9 | | 9 | 8 | 9 | 9 | 7 | 9 | 6 | 8 | 7 | 9 | |
| 6-cyclohexyl-8-methyl-imidazo-[1,5-d]-as-triazin-4(3H)-one | 2.24 | | 9 | | 0 | 9 | 9 | 3 | 9 | 7 | 0 | 5 | 6 | 9 |
| | 1.12 | | 2 | | 0 | 0 | 9 | 0 | 5 | 6 | 0 | 0 | 3 | 3 |
| | 0.56 | | 2 | | 0 | 0 | 9 | 0 | 5 | 0 | 0 | 0 | 2 | 3 |
| 6-n-hexyl-8-methyl-imidazo[1,5-d]-as-triazin-4(3H)-one | 11.2 | 9 | | 9 | 9 | 9 | 9 | 9 | 9 | 9 | 9 | 9 | 9 | |
| | 2.24 | | 9 | | 9 | 9 | 9 | 9 | 9 | 9 | 5 | 5 | 9 | 9 |
| | 1.12 | | 5 | | 5 | 3 | 9 | 0 | 5 | 5 | 0 | 0 | 3 | 2 |
| | 0.56 | | 3 | | 2 | 1 | 3 | 0 | 0 | 2 | 0 | 0 | 2 | 0 |
| 8-methyl-6-(m-tolyl)-imidazo- | 11.2 | 9 | | 9 | 9 | 9 | 9 | 9 | 9 | 9 | 9 | 9 | 9 | |
| | 2.24 | | 9 | | 9 | 9 | 9 | 0 | 3 | 7 | 5 | 3 | 6 | 9 |
| | 1.12 | | 9 | | 9 | 9 | 9 | 0 | 3 | 2 | 2 | 0 | 5 | 0 |
| | 0.56 | | 9 | | 9 | 9 | 9 | 0 | 0 | 0 | 0 | 0 | 3 | 0 |
| | 0.28 | | 7 | | 9 | 3 | 9 | 0 | 0 | 0 | 0 | 0 | 2 | 0 |
| 8-methyl-6-(o-tolyl)-imidazo-[1,5-d]-as-triazin-4(3H)-one | 11.2 | 3 | | 5 | 9 | 2 | 2 | 3 | 8 | 7 | 5 | 5 | 5 | |
| | 2.24 | | 2 | | 3 | 0 | 0 | 3 | 0 | 0 | 0 | 5 | 0 | |
| | 1.12 | | 9* | | 9* | 9* | 9* | 9* | 9* | 7* | 7* | 6* | 7* | 9* |
| 8-iodo-6-phenyl-imidazo[1,5-d]-as-triazin-4(3H)-one | 0.56 | | 9* | | 9* | 9* | 6* | 9* | 8* | 6* | 4.5* | 5.5* | 5* | 8* |
| | 0.28 | | 9* | | 9* | 7* | 3* | 5* | 5.5* | 2.5* | 2.5* | 2.5* | 3.5* | 7* |
| | 0.14 | | 6* | | 8* | 4.5* | 1* | 3* | 1* | 1.5* | 1.5* | 1.5* | 1.5* | 7.5* |
| | 2.24 | | 0 | | 9 | 7 | 2 | 0 | 0 | 0 | 0 | 0 | 0 | |
| 8-bromo-6-(m-aminophenyl)-imidazo-[1,5-d]-as-triazin-4(3H)-one | 1.12 | | 0 | | 9 | 0 | 0 | 0 | 0 | 0 | 0 | 0 | 0 | |
| | 0.56 | | 0 | | 9 | 0 | 0 | 0 | 0 | 0 | 0 | 0 | 0 | |
| | 0.28 | | 0 | | 2 | 0 | 0 | 0 | 0 | 0 | 0 | 0 | 0 | |

*Average of two or more replicates

I claim:

1. A method for the pre- and postemergence control of monocotyledonous and dicotyledonous plant species comprising: applying to the foliage of said plants or to the soil in which said plants or seeds germinate and propagate, a herbicidally effective amount of a compound of the formula:

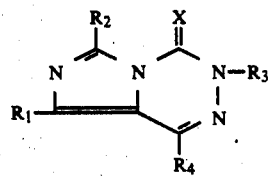

wherein X is oxygen or sulfur; $R_1$ is a member selected from the group consisting of hydrogen, alkyl $C_1$-$C_3$, bromo, chloro, and iodo; $R_2$ is a member selected from the group consisting of hydrogen, alkyl $C_1$-$C_6$, cycloalkyl $C_3$-$C_6$, naphthyl, phenyl and monosubstituted phenyl wherein said substituent is selected from the group consisting of halogen, alkyl $C_1$-$C_4$, alkoxy $C_1$-$C_4$, haloalkyl $C_1$-$C_3$, dimethylamino and nitro; $R_3$ is hydrogen, alkyl $C_1$-$C_3$, alkenyl $C_3$-$C_4$ and alkynyl $C_3$-$C_4$, and $R_4$ is hydrogen or alkyl $C_1$-$C_4$.

2. The method according to claim 1 wherein X is oxygen; $R_1$ is methyl, bromo or chloro; $R_2$ is cycloalkyl $C_3$-$C_6$, phenyl or m-tolyl; $R_3$ and $R_4$ are both hydrogen.

3. The method according to claim 1, wherein said compound is 8-methyl-6-phenyl-imidazo[1,5-d]-as-triazin-4(3H)-one.

4. The method according to claim 1, wherein said compound is 8-bromo-6-phenyl-imidazo[1,5-d]-as-triazin-4(3H)-one.

5. The method according to claim 1 wherein said compound is 8-chloro-6-phenyl-imidazo[1,5-d]-as-triazin-4(3H)-one.

6. The method according to claim 1 wherein said compound is 6-cyclohexyl-8-methyl-imidazo[1,5-d]-as-triazin-4(3H)-one.

7. The method according to claim 1 wherein said compound is 8-methyl-6-m-tolyl-imidazo[1,5-d]-as-triazin-4(3H)-one.

8. The method according to claim 1 wherein said compound is 6-phenyl-imidazo[1,5-d]-as-triazin-4(3H)-one.

9. The method according to claim 1 wherein said compound is 8-iodo-6-phenyl-imidazo[1,5-d]-as-triazin-4(3H)-one.

10. The method according to claim 1 wherein said compound is 8-methyl-6-n-propyl-imidazo[1,5-d]-as-triazin-4(3H)-one.

11. The method according to claim 1 wherein said compound is 8-methyl-6-n-propyl-imidazo[1,5-d]-as-triazin-4(3H)-thione.

12. The method according to claim 1 wherein the compound is 8-methyl-6-(α,α,α-trifluoro-m-tolyl)-imidazo[1,5-d]-as-triazin-4(3H)-one.

13. The method according to claim 1 wherein said compound is applied at from 0.07 to 11.2 kg per hectare.

* * * * *